United States Patent
Wachman et al.

(10) Patent No.: US 12,014,328 B2
(45) Date of Patent: Jun. 18, 2024

(54) MEDICINE BOTTLE CAP WITH ELECTRONIC EMBEDDED CURVED DISPLAY

(75) Inventors: Joshua Seth Wachman, Newton, MA (US); David Loring Rose, Brookline, MA (US)

(73) Assignee: VCCB Holdings, Inc., Wilmington, DE (US)

( * ) Notice: Subject to any disclaimer, the term of this patent is extended or adjusted under 35 U.S.C. 154(b) by 620 days.

(21) Appl. No.: 12/770,436

(22) Filed: Apr. 29, 2010

(65) Prior Publication Data

US 2010/0270257 A1 Oct. 28, 2010

Related U.S. Application Data

(63) Continuation-in-part of application No. 11/480,859, filed on Jul. 6, 2006, now abandoned, and a continuation-in-part of application No. 12/352,647, filed on Jan. 13, 2009, now abandoned, which is a continuation-in-part of application No. 11/480,859, filed on Jul. 6, 2006, now abandoned.

(60) Provisional application No. 61/174,045, filed on Apr. 30, 2009, provisional application No. 60/698,792, filed on Jul. 13, 2005.

(51) Int. Cl.
*G06Q 10/10* (2023.01)
*G16H 20/13* (2018.01)

(52) U.S. Cl.
CPC .......... *G06Q 10/10* (2013.01); *G16H 20/13* (2018.01)

(58) Field of Classification Search
CPC ........ G06Q 10/00; G06Q 50/00; G06Q 10/10; G16H 10/00; G16H 15/00; G16H 20/00; G16H 30/00; G16H 40/00; G16H 50/00; G16H 70/00; G16H 80/00; G16H 10/40; G16H 20/10; G16H 20/13; G16H 20/17; G06F 19/3462
USPC .................................................. 705/2, 3, 20
See application file for complete search history.

(56) References Cited

U.S. PATENT DOCUMENTS

D169,266 S 4/1953 Lehman
D207,887 S 6/1967 Parisson et al.
(Continued)

FOREIGN PATENT DOCUMENTS

EP 0 298 627 1/1989
EP 0 265 049 1/1993
(Continued)

OTHER PUBLICATIONS

Final Office Action in U.S. Appl. No. 11/480,859 dated Sep. 4, 2015.
(Continued)

*Primary Examiner* — Robert W Morgan
*Assistant Examiner* — Charles P Coleman
(74) *Attorney, Agent, or Firm* — Knobbe, Martens, Olson & Bear, LLP

(57) ABSTRACT

A cap for a medicine container includes a base portion having a curved outer surface and being connectable to a medicine container, the base having an indented portion on at least a part of said curved outer surface. An electronic display fits in the indented portion of the base portion and electronically connected to circuitry within the cap. A clear portion covers the electronic display. A multi-color light-emitting diode (LED) electronically connected to the circuitry within the cap.

20 Claims, 27 Drawing Sheets

(56) References Cited

U.S. PATENT DOCUMENTS

| | | | |
|---|---|---|---|
| 3,990,558 A | 11/1976 | Ehrat | |
| 4,034,757 A | 7/1977 | Glover | |
| 4,223,801 A | 9/1980 | Carlson | |
| D257,229 S * | 10/1980 | Leger | D9/443 |
| 4,347,804 A | 9/1982 | Villa-Real | |
| 4,361,408 A | 11/1982 | Wirtschafter | |
| 4,367,955 A | 1/1983 | Ballew | |
| 4,419,016 A | 12/1983 | Zoltan | |
| 4,473,156 A | 9/1984 | Martia | |
| 4,489,834 A | 12/1984 | Thackrey | |
| 4,504,153 A | 3/1985 | Schollmeyer et al. | |
| 4,526,474 A | 7/1985 | Simon | |
| 4,572,403 A | 2/1986 | Benaroya | |
| 4,588,303 A | 5/1986 | Wirtschafter et al. | |
| 4,616,316 A | 10/1986 | Hanpeter et al. | |
| 4,658,093 A | 4/1987 | Hellman | |
| 4,666,160 A | 5/1987 | Hamilton | |
| 4,695,954 A | 9/1987 | Rose et al. | |
| 4,725,997 A | 2/1988 | Urquhart et al. | |
| 4,731,726 A | 3/1988 | Allen, III | |
| 4,748,600 A | 5/1988 | Urquhart | |
| 4,768,176 A | 8/1988 | Kehr et al. | |
| 4,768,177 A | 8/1988 | Kehr et al. | |
| 4,782,966 A | 11/1988 | Thackrey | |
| 4,786,940 A | 11/1988 | Daniele | |
| 4,803,625 A | 2/1989 | Fu et al. | |
| 4,831,438 A | 5/1989 | Bellman, Jr. et al. | |
| 4,839,806 A | 6/1989 | Goldfischer et al. | |
| 4,899,839 A | 2/1990 | Dessertine et al. | |
| 4,905,213 A | 2/1990 | Masse et al. | |
| 4,933,873 A | 6/1990 | Kaufman et al. | |
| 4,939,705 A | 7/1990 | Hamilton et al. | |
| 4,942,544 A | 7/1990 | McIntosh | |
| 4,960,128 A | 10/1990 | Gordon et al. | |
| 4,964,408 A | 10/1990 | Hink et al. | |
| 4,964,683 A | 10/1990 | Sugarek et al. | |
| 4,971,221 A | 11/1990 | Urquhart | |
| 5,001,752 A | 3/1991 | Fischer | |
| 5,009,338 A | 4/1991 | Barker | |
| 5,014,798 A | 5/1991 | Glynn | |
| 5,016,172 A | 5/1991 | Dessertine | |
| 5,016,230 A | 5/1991 | Seifers et al. | |
| 5,020,037 A | 5/1991 | Raven | |
| 5,022,080 A | 6/1991 | Durst et al. | |
| 5,027,395 A | 6/1991 | Anderson et al. | |
| 5,036,461 A | 7/1991 | Elliott et al. | |
| 5,050,212 A | 9/1991 | Dyson | |
| 5,073,931 A | 12/1991 | Audebert et al. | |
| 5,075,862 A | 12/1991 | Doeberl et al. | |
| 5,083,271 A | 1/1992 | Thacher et al. | |
| 5,088,056 A | 2/1992 | McIntosh et al. | |
| 5,112,051 A | 5/1992 | Darling et al. | |
| D327,430 S * | 6/1992 | Farricielli | D9/443 |
| 5,136,646 A | 8/1992 | Haber et al. | |
| 5,136,647 A | 8/1992 | Haber et al. | |
| 5,142,484 A | 8/1992 | Kaufman et al. | |
| D329,980 S | 10/1992 | Powell et al. | |
| 5,155,680 A | 10/1992 | Wiedemer | |
| 5,157,726 A | 10/1992 | Merkle et al. | |
| 5,189,700 A | 2/1993 | Blandford | |
| 5,193,114 A | 3/1993 | Moseley | |
| 5,200,891 A | 4/1993 | Kehr et al. | |
| 5,202,923 A | 4/1993 | Kuriyama | |
| 5,216,975 A | 6/1993 | Bartholomew | |
| 5,233,571 A | 8/1993 | Wirtschafter | |
| 5,243,652 A | 9/1993 | Teare et al. | |
| 5,243,654 A | 9/1993 | Hunter | |
| 5,259,029 A | 11/1993 | Duncan, Jr. | |
| 5,271,353 A | 12/1993 | Besthorne | |
| 5,288,978 A | 2/1994 | Iijima | |
| 5,289,157 A | 2/1994 | Rudick et al. | |
| 5,297,205 A | 3/1994 | Audebert et al. | |
| 5,299,701 A | 4/1994 | Barker et al. | |
| 5,309,145 A | 5/1994 | Branch et al. | |
| 5,313,439 A | 5/1994 | Albeck | |
| 5,319,355 A | 6/1994 | Russek | |
| 5,319,710 A | 6/1994 | Atalla et al. | |
| 5,337,744 A | 8/1994 | Branigan | |
| 5,341,805 A | 8/1994 | Stavridi et al. | |
| 5,347,579 A | 9/1994 | Blandford | |
| 5,347,580 A | 9/1994 | Molva et al. | |
| 5,349,642 A | 9/1994 | Kingdon | |
| 5,351,293 A | 9/1994 | Michener et al. | |
| 5,355,413 A | 10/1994 | Ohno | |
| 5,358,117 A | 10/1994 | Adams | |
| 5,359,510 A | 10/1994 | Sabaliauskas | |
| D353,195 S | 12/1994 | Savage et al. | |
| D353,196 S | 12/1994 | Savage et al. | |
| 5,372,276 A | 12/1994 | Daneshvar | |
| 5,377,268 A | 12/1994 | Hunter | |
| 5,377,614 A | 1/1995 | Glazer | |
| 5,377,676 A | 1/1995 | Vari et al. | |
| 5,386,468 A | 1/1995 | Akiyama et al. | |
| 5,392,952 A | 2/1995 | Bowden | |
| 5,400,319 A | 3/1995 | Fite et al. | |
| 5,408,443 A | 4/1995 | Weinberger | |
| RE34,954 E | 5/1995 | Haber et al. | |
| 5,412,372 A | 5/1995 | Parkhurst et al. | |
| 5,412,575 A | 5/1995 | Constant et al. | |
| 5,416,840 A | 5/1995 | Cane et al. | |
| D359,546 S | 6/1995 | Savage et al. | |
| 5,431,170 A | 7/1995 | Mathews | |
| 5,433,324 A | 7/1995 | Leonard | |
| 5,434,918 A | 7/1995 | Kung et al. | |
| 5,436,499 A | 7/1995 | Namavar et al. | |
| D361,840 S | 8/1995 | Savage et al. | |
| D362,063 S | 9/1995 | Savage et al. | |
| D363,120 S | 10/1995 | Savage et al. | |
| 5,456,252 A | 10/1995 | Vari et al. | |
| 5,468,948 A | 11/1995 | Koenck et al. | |
| 5,472,113 A | 12/1995 | Shaw | |
| 5,479,934 A | 1/1996 | Imran | |
| 5,482,036 A | 1/1996 | Diab et al. | |
| 5,494,043 A | 2/1996 | O'Sullivan et al. | |
| 5,497,419 A | 3/1996 | Hill | |
| 5,499,294 A | 3/1996 | Friedman | |
| 5,508,731 A | 4/1996 | Kohorn | |
| 5,533,511 A | 7/1996 | Kaspari et al. | |
| 5,539,822 A | 7/1996 | Lett | |
| D374,623 S | 10/1996 | Rafferty | |
| 5,561,275 A | 10/1996 | Savage et al. | |
| 5,569,082 A | 10/1996 | Kaye | |
| 5,583,831 A | 12/1996 | Churchill et al. | |
| 5,590,649 A | 1/1997 | Caro et al. | |
| 5,602,802 A | 2/1997 | Leigh-Spencer et al. | |
| 5,602,924 A | 2/1997 | Durand et al. | |
| 5,619,991 A | 4/1997 | Sloane | |
| 5,625,334 A | 4/1997 | Compton | |
| 5,625,347 A | 4/1997 | MacLean et al. | |
| 5,638,816 A | 6/1997 | Kiani-Azarbayjany et al. | |
| 5,638,818 A | 6/1997 | Diab et al. | |
| 5,641,091 A | 6/1997 | Daneshvar | |
| 5,642,731 A | 7/1997 | Kehr | |
| 5,645,440 A | 7/1997 | Tobler et al. | |
| 5,646,912 A | 7/1997 | Cousin | |
| 5,646,994 A | 7/1997 | Hill | |
| 5,671,914 A | 9/1997 | Kalkhoran et al. | |
| D385,491 S * | 10/1997 | Mueller | D9/443 |
| 5,678,571 A | 10/1997 | Brown | |
| 5,706,257 A | 1/1998 | Rothman et al. | |
| 5,710,551 A | 1/1998 | Ridgeway | |
| 5,726,440 A | 3/1998 | Kalkhoran et al. | |
| D393,830 S | 4/1998 | Tobler et al. | |
| 5,743,262 A | 4/1998 | Lepper, Jr. et al. | |
| 5,747,806 A | 5/1998 | Khalil et al. | |
| 5,750,994 A | 5/1998 | Schlager | |
| 5,751,661 A | 5/1998 | Walters | |
| 5,752,235 A | 5/1998 | Kehr et al. | |
| 5,758,644 A | 6/1998 | Diab et al. | |
| 5,760,910 A | 6/1998 | Lepper, Jr. et al. | |
| 5,768,382 A | 6/1998 | Schneier et al. | |
| 5,774,865 A | 6/1998 | Glynn | |
| 5,779,549 A | 7/1998 | Walker et al. | |
| 5,793,653 A | 8/1998 | Segal | |

(56) References Cited

U.S. PATENT DOCUMENTS

| | | | |
|---|---|---|---|
| 5,794,207 A | 8/1998 | Walker et al. |
| 5,800,264 A | 9/1998 | Pascal et al. |
| 5,805,051 A | 9/1998 | Herrmann |
| 5,815,586 A | 9/1998 | Dobbins |
| 5,823,346 A | 10/1998 | Weiner |
| 5,827,180 A | 10/1998 | Goodman |
| 5,828,751 A | 10/1998 | Walker et al. |
| 5,850,344 A | 12/1998 | Conkright |
| 5,850,447 A | 12/1998 | Peyret |
| 5,852,590 A | 12/1998 | de la Huerga |
| 5,867,821 A | 2/1999 | Ballantyne et al. |
| 5,871,398 A | 2/1999 | Schneier et al. |
| 5,883,576 A | 3/1999 | de la Huerga |
| 5,890,929 A | 4/1999 | Mills et al. |
| 5,897,493 A | 4/1999 | Brown |
| 5,899,855 A | 5/1999 | Brown |
| 5,902,234 A | 5/1999 | Webb |
| D411,451 S | 6/1999 | Young |
| 5,917,429 A | 6/1999 | Otis, Jr. et al. |
| 5,919,134 A | 7/1999 | Diab |
| 5,923,763 A | 7/1999 | Walker et al. |
| 5,950,632 A | 9/1999 | Reber |
| 5,953,288 A | 9/1999 | Chappell |
| 5,954,641 A | 9/1999 | Kehr et al. |
| 5,960,085 A | 9/1999 | de la Huerga |
| 5,960,403 A | 9/1999 | Brown |
| 5,970,143 A | 10/1999 | Schneier et al. |
| 5,974,389 A | 10/1999 | Clark |
| 5,987,343 A | 11/1999 | Kinast |
| 5,997,343 A | 12/1999 | Mills et al. |
| 5,997,476 A | 12/1999 | Brown |
| 6,002,952 A | 12/1999 | Diab et al. |
| 6,010,937 A | 1/2000 | Karam et al. |
| 6,018,289 A | 1/2000 | Sekura et al. |
| 6,021,392 A | 2/2000 | Lester et al. |
| 6,024,699 A | 2/2000 | Surwit et al. |
| 6,027,452 A | 2/2000 | Flaherty et al. |
| 6,032,155 A | 2/2000 | De La Huerga |
| 6,032,609 A | 3/2000 | Luoma |
| 6,039,688 A | 3/2000 | Douglas et al. |
| 6,040,578 A | 3/2000 | Malin et al. |
| 6,066,204 A | 5/2000 | Haven |
| 6,075,755 A | 6/2000 | Zarchan |
| 6,084,504 A | 7/2000 | Rosche et al. |
| 6,088,429 A | 7/2000 | Garcia |
| 6,101,478 A | 8/2000 | Brown |
| 6,102,855 A | 8/2000 | Kehr et al. |
| 6,115,673 A | 9/2000 | Malin et al. |
| 6,124,597 A | 9/2000 | Shehada et al. |
| 6,128,521 A | 10/2000 | Marro et al. |
| 6,129,675 A | 10/2000 | Jay |
| 6,142,910 A | 11/2000 | Heuvelman |
| 6,144,868 A | 11/2000 | Parker |
| 6,150,942 A * | 11/2000 | O'Brien ................... 340/573.1 |
| 6,152,067 A | 11/2000 | Mathison |
| 6,152,754 A | 11/2000 | Gerhardt et al. |
| 6,158,613 A | 12/2000 | Novosel et al. |
| 6,161,095 A | 12/2000 | Brown |
| 6,167,362 A | 12/2000 | Brown et al. |
| 6,168,563 B1 | 1/2001 | Brown |
| 6,183,417 B1 | 2/2001 | Geheb et al. |
| 6,184,521 B1 | 2/2001 | Coffin, IV et al. |
| 6,221,010 B1 | 4/2001 | Lucas |
| 6,229,431 B1 | 5/2001 | Weiner |
| 6,232,609 B1 | 5/2001 | Snyder et al. |
| 6,236,953 B1 | 5/2001 | Segal |
| 6,239,712 B1 | 5/2001 | Hawk |
| 6,241,683 B1 | 6/2001 | Macklem et al. |
| 6,255,708 B1 | 7/2001 | Sudharsanan et al. |
| 6,255,951 B1 | 7/2001 | de la Huerga |
| 6,259,356 B1 | 7/2001 | Tamaoki et al. |
| 6,259,654 B1 | 7/2001 | de la Huerga |
| 6,271,753 B1 | 8/2001 | Shukla |
| 6,272,481 B1 | 8/2001 | Lawrence et al. |
| 6,280,381 B1 | 8/2001 | Malin et al. |
| 6,285,896 B1 | 9/2001 | Tobler et al. |
| 6,285,916 B1 | 9/2001 | Kadaba et al. |
| 6,294,999 B1 | 9/2001 | Yarin et al. |
| 6,302,295 B1 | 10/2001 | Weisman |
| 6,308,089 B1 | 10/2001 | von der Ruhr et al. |
| D451,021 S * | 11/2001 | Berge ........................ D9/445 |
| 6,314,384 B1 | 11/2001 | Goetz |
| 6,317,390 B1 | 11/2001 | Cardoza |
| 6,317,627 B1 | 11/2001 | Ennen et al. |
| 6,321,100 B1 | 11/2001 | Parker |
| 6,324,123 B1 | 11/2001 | Durso |
| 6,332,100 B1 | 12/2001 | Sahai et al. |
| 6,334,065 B1 | 12/2001 | Al-Ali et al. |
| 6,335,907 B1 | 1/2002 | Momich et al. |
| 6,346,886 B1 | 2/2002 | de la Huerga |
| 6,356,192 B1 | 3/2002 | Menard et al. |
| 6,360,114 B1 | 3/2002 | Diab et al. |
| 6,366,206 B1 | 4/2002 | Ishikawa et al. |
| 6,368,283 B1 | 4/2002 | Xu et al. |
| 6,375,614 B1 | 4/2002 | Braun |
| 6,380,858 B1 | 4/2002 | Yarin et al. |
| 6,408,330 B1 | 6/2002 | de la Huerga |
| 6,411,373 B1 | 6/2002 | Garside et al. |
| 6,415,167 B1 | 7/2002 | Blank et al. |
| 6,424,599 B1 | 7/2002 | Ditzig |
| 6,430,437 B1 | 8/2002 | Marro |
| 6,430,525 B1 | 8/2002 | Weber et al. |
| 6,463,311 B1 | 10/2002 | Diab |
| 6,470,199 B1 | 10/2002 | Kopotic et al. |
| 6,487,429 B2 | 11/2002 | Hockersmith et al. |
| 6,505,059 B1 | 1/2003 | Kollias et al. |
| 6,525,386 B1 | 2/2003 | Mills et al. |
| 6,526,300 B1 | 2/2003 | Kiani et al. |
| 6,529,486 B1 | 3/2003 | de la Huerga |
| 6,529,876 B1 * | 3/2003 | Dart et al. ........................ 705/4 |
| 6,534,012 B1 | 3/2003 | Hazen et al. |
| 6,542,764 B1 | 4/2003 | Al-Ali et al. |
| 6,563,910 B2 | 5/2003 | Menard et al. |
| 6,564,121 B1 | 5/2003 | Wallace et al. |
| 6,578,003 B1 | 6/2003 | Camarda et al. |
| 6,580,086 B1 | 6/2003 | Schulz et al. |
| 6,584,336 B1 | 6/2003 | Ali et al. |
| 6,587,196 B1 | 7/2003 | Stippick et al. |
| 6,587,199 B1 | 7/2003 | Luu |
| 6,589,169 B1 | 7/2003 | Surwit et al. |
| 6,594,549 B2 | 7/2003 | Siegel |
| 6,595,316 B2 | 7/2003 | Cybulski et al. |
| 6,597,932 B2 | 7/2003 | Tian et al. |
| 6,604,650 B2 | 8/2003 | Sagar |
| 6,606,511 B1 | 8/2003 | Ali et al. |
| 6,608,557 B1 | 8/2003 | Menard et al. |
| 6,633,796 B1 | 10/2003 | Pool et al. |
| 6,635,559 B2 | 10/2003 | Greenwald et al. |
| 6,636,780 B1 | 10/2003 | Haitin et al. |
| 6,639,668 B1 | 10/2003 | Trepagnier |
| 6,640,116 B2 | 10/2003 | Diab |
| 6,640,117 B2 | 10/2003 | Makarewicz et al. |
| 6,658,276 B2 | 12/2003 | Kiani et al. |
| 6,661,161 B1 | 12/2003 | Lanzo et al. |
| 6,662,081 B1 | 12/2003 | Jacober et al. |
| 6,664,944 B1 * | 12/2003 | Albert et al. ................. 345/107 |
| 6,667,688 B1 | 12/2003 | Menard et al. |
| 6,667,936 B1 | 12/2003 | Ditzig |
| 6,671,351 B2 | 12/2003 | Menard et al. |
| 6,680,999 B1 | 1/2004 | Garcia |
| 6,697,656 B1 | 2/2004 | Al-Ali |
| 6,697,658 B2 | 2/2004 | Al-Ali |
| RE38,476 E | 3/2004 | Diab et al. |
| 6,702,146 B2 | 3/2004 | Varis |
| 6,707,763 B2 | 3/2004 | Osberg et al. |
| 6,710,703 B2 | 3/2004 | Huang |
| RE38,492 E | 4/2004 | Diab et al. |
| 6,727,818 B1 | 4/2004 | Wildman et al. |
| 6,728,341 B1 | 4/2004 | Puchek |
| 6,738,652 B2 | 5/2004 | Mattu et al. |
| 6,751,730 B1 | 6/2004 | Walker et al. |
| 6,759,956 B2 | 7/2004 | Menard et al. |
| 6,759,959 B2 | 7/2004 | Wildman |
| 6,760,607 B2 | 7/2004 | Al-Ali |

(56) References Cited

U.S. PATENT DOCUMENTS

| | | |
|---|---|---|
| 6,765,478 B2 | 7/2004 | Zhurin |
| 6,771,165 B2 | 8/2004 | Burg, II et al. |
| 6,771,174 B2 | 8/2004 | Broas |
| 6,788,965 B2 | 9/2004 | Ruchti et al. |
| 6,816,241 B2 | 11/2004 | Grubisic |
| 6,822,554 B2 | 11/2004 | Vrijens et al. |
| 6,822,564 B2 | 11/2004 | Al-Ali |
| 6,832,916 B2 | 12/2004 | Collopy |
| 6,847,293 B2 | 1/2005 | Menard et al. |
| 6,850,787 B2 | 2/2005 | Weber et al. |
| 6,850,788 B2 | 2/2005 | Al-Ali |
| 6,875,174 B2 | 4/2005 | Braun et al. |
| 6,876,931 B2 | 4/2005 | Lorenz et al. |
| 6,877,626 B2 | 4/2005 | Sherrod |
| 6,894,609 B2 | 5/2005 | Menard et al. |
| 6,912,399 B2 | 6/2005 | Zirul et al. |
| 6,920,345 B2 | 7/2005 | Al-Ali et al. |
| 6,934,570 B2 | 8/2005 | Kiani et al. |
| 6,943,348 B1 | 9/2005 | Coffin, IV |
| 6,953,039 B2 | 10/2005 | Scarrott et al. |
| 6,956,649 B2 | 10/2005 | Acosta et al. |
| 6,960,998 B2 | 11/2005 | Menard et al. |
| 6,961,285 B2 | 11/2005 | Niemiec et al. |
| 6,961,598 B2 | 11/2005 | Diab |
| 6,967,562 B2 | 11/2005 | Menard et al. |
| 6,968,375 B1 | 11/2005 | Brown |
| 6,970,792 B1 | 11/2005 | Diab |
| 6,980,958 B1 | 12/2005 | Surwit et al. |
| 6,985,764 B2 | 1/2006 | Mason et al. |
| 6,985,870 B2 | 1/2006 | Martucci et al. |
| 6,990,364 B2 | 1/2006 | Ruchti et al. |
| 6,998,247 B2 | 2/2006 | Monfre et al. |
| 7,002,476 B2 | 2/2006 | Rapchak |
| 7,003,338 B2 | 2/2006 | Weber et al. |
| 7,010,369 B2 | 3/2006 | Borders et al. |
| 7,015,451 B2 | 3/2006 | Dalke et al. |
| 7,015,816 B2 | 3/2006 | Wildman et al. |
| 7,027,849 B2 | 4/2006 | Al-Ali |
| D521,863 S | 5/2006 | Davis et al. |
| 7,041,468 B2 | 5/2006 | Drucker et al. |
| 7,080,755 B2 | 7/2006 | Handfield et al. |
| 7,081,807 B2 | 7/2006 | Lai |
| D526,719 S | 8/2006 | Richie, Jr. et al. |
| 7,088,233 B2 | 8/2006 | Menard |
| 7,096,052 B2 | 8/2006 | Mason et al. |
| 7,096,054 B2 | 8/2006 | Abdul-Hafiz et al. |
| 7,103,344 B2 | 9/2006 | Menard |
| D529,616 S | 10/2006 | Deros et al. |
| D531,030 S * | 10/2006 | Nukuto .................. D9/445 |
| 7,116,223 B2 | 10/2006 | Stern et al. |
| 7,119,688 B2 | 10/2006 | Wildman |
| 7,133,710 B2 | 11/2006 | Acosta et al. |
| 7,138,902 B2 | 11/2006 | Menard |
| 7,138,906 B2 | 11/2006 | Rosche |
| 7,142,901 B2 | 11/2006 | Kiani et al. |
| 7,167,818 B2 | 1/2007 | Brown |
| 7,223,235 B2 | 5/2007 | Brown |
| 7,223,236 B2 | 5/2007 | Brown |
| 7,225,006 B2 | 5/2007 | Al-Ali et al. |
| RE39,672 E | 6/2007 | Shehada et al. |
| 7,252,636 B2 | 8/2007 | Brown |
| 7,254,429 B2 | 8/2007 | Schurman et al. |
| 7,254,431 B2 | 8/2007 | Al-Ali et al. |
| 7,254,434 B2 | 8/2007 | Schulz et al. |
| 7,258,666 B2 | 8/2007 | Brown |
| 7,260,480 B1 | 8/2007 | Brown et al. |
| 7,264,591 B2 | 9/2007 | Brown |
| 7,274,955 B2 | 9/2007 | Kiani et al. |
| D554,263 S | 10/2007 | Al-Ali et al. |
| 7,280,858 B2 | 10/2007 | Al-Ali et al. |
| 7,289,016 B2 | 10/2007 | Luebke et al. |
| 7,289,835 B2 | 10/2007 | Mansfield et al. |
| 7,292,883 B2 | 11/2007 | De Felice et al. |
| 7,295,890 B2 | 11/2007 | Jean-Pierre |
| 7,297,109 B2 | 11/2007 | Brown |
| 7,299,192 B2 | 11/2007 | Luttrell |
| 7,304,582 B2 | 12/2007 | Kerr, II et al. |
| 7,305,348 B1 | 12/2007 | Brown |
| 7,310,668 B2 | 12/2007 | Brown |
| 7,320,030 B2 | 1/2008 | Brown |
| 7,341,559 B2 | 3/2008 | Schulz et al. |
| 7,343,186 B2 | 3/2008 | Lamego et al. |
| D566,282 S | 4/2008 | Al-Ali et al. |
| 7,356,365 B2 | 4/2008 | Schurman |
| 7,362,660 B2 | 4/2008 | Hildebrandt |
| 7,366,675 B1 | 4/2008 | Walker et al. |
| 7,369,919 B2 | 5/2008 | Vonk |
| 7,371,981 B2 | 5/2008 | Abdul-Hafiz |
| 7,373,193 B2 | 5/2008 | Al-Ali et al. |
| 7,377,794 B2 | 5/2008 | Al-Ali et al. |
| 7,378,976 B1 | 5/2008 | Paterno |
| 7,382,692 B1 | 6/2008 | Hildebrandt |
| 7,392,167 B2 | 6/2008 | Brown |
| 7,394,383 B2 | 7/2008 | Hager et al. |
| 7,395,158 B2 | 7/2008 | Monfre et al. |
| 7,399,276 B1 | 7/2008 | Brown et al. |
| 7,408,470 B2 | 8/2008 | Wildman et al. |
| 7,415,297 B2 | 8/2008 | Al-Ali et al. |
| D578,391 S | 10/2008 | Larkin et al. |
| 7,438,683 B2 | 10/2008 | Al-Ali et al. |
| 7,440,818 B2 | 10/2008 | Handfield et al. |
| 7,443,303 B2 | 10/2008 | Spear et al. |
| 7,483,729 B2 | 1/2009 | Al-Ali et al. |
| D587,657 S | 3/2009 | Al-Ali et al. |
| 7,500,950 B2 | 3/2009 | Al-Ali et al. |
| 7,502,666 B2 | 3/2009 | Siegel et al. |
| 7,504,954 B2 | 3/2009 | Spaeder |
| 7,509,494 B2 | 3/2009 | Al-Ali |
| 7,510,849 B2 | 3/2009 | Schurman et al. |
| 7,514,725 B2 | 4/2009 | Wojtczuk et al. |
| 7,516,192 B2 | 4/2009 | Brown |
| 7,519,406 B2 | 4/2009 | Blank et al. |
| D592,507 S | 5/2009 | Wachman et al. |
| 7,530,942 B1 | 5/2009 | Diab |
| 7,533,171 B2 | 5/2009 | Brown |
| 7,553,234 B2 | 6/2009 | Walker et al. |
| 7,553,235 B2 | 6/2009 | Walker et al. |
| 7,555,436 B2 | 6/2009 | Brown |
| 7,584,108 B2 | 9/2009 | Brown |
| 7,587,287 B2 | 9/2009 | Connolly et al. |
| 7,587,469 B2 | 9/2009 | Brown |
| 7,590,549 B2 | 9/2009 | Brown |
| 7,593,230 B2 | 9/2009 | Abul-Haj et al. |
| 7,596,398 B2 | 9/2009 | Al-Ali et al. |
| 7,602,275 B2 | 10/2009 | Dishongh et al. |
| 7,606,608 B2 | 10/2009 | Blank et al. |
| 7,607,442 B2 | 10/2009 | Barnhill et al. |
| 7,607,443 B2 | 10/2009 | Barnhill et al. |
| 7,612,662 B2 | 11/2009 | Niemiec et al. |
| 7,613,590 B2 | 11/2009 | Brown |
| 7,613,621 B2 | 11/2009 | Brown |
| 7,617,830 B2 | 11/2009 | Barnhill et al. |
| 7,620,438 B2 | 11/2009 | He |
| 7,620,674 B2 | 11/2009 | Ruchti et al. |
| 7,624,028 B1 | 11/2009 | Brown |
| D606,659 S | 12/2009 | Kiani et al. |
| 7,629,039 B2 | 12/2009 | Eckerbom et al. |
| 7,630,790 B2 | 12/2009 | Handfield et al. |
| 7,640,140 B2 | 12/2009 | Ruchti et al. |
| 7,641,740 B2 | 1/2010 | Barnhill et al. |
| 7,643,971 B2 | 1/2010 | Brown |
| 7,647,083 B2 | 1/2010 | Al-Ali et al. |
| D609,193 S | 2/2010 | Al-Ali et al. |
| 7,659,824 B2 | 2/2010 | Prodanovich et al. |
| 7,663,977 B1 | 2/2010 | Hartelius |
| 7,682,464 B2 | 3/2010 | Glenn et al. |
| 7,689,440 B2 | 3/2010 | Brown |
| D614,305 S | 4/2010 | Al-Ali et al. |
| 7,697,966 B2 | 4/2010 | Monfre et al. |
| 7,698,105 B2 | 4/2010 | Ruchti et al. |
| 7,698,770 B2 | 4/2010 | Barnhill et al. |
| 7,707,270 B2 | 4/2010 | Brown |
| RE41,317 E | 5/2010 | Parker |
| RE41,333 E | 5/2010 | Blank et al. |

(56) References Cited

U.S. PATENT DOCUMENTS

| | | |
|---|---|---|
| 7,729,733 B2 | 6/2010 | Al-Ali et al. |
| 7,734,718 B2 | 6/2010 | Brown |
| 7,739,130 B2 | 6/2010 | Surwit et al. |
| 7,754,021 B2 | 7/2010 | Barnhill et al. |
| 7,754,022 B2 | 7/2010 | Barnhill et al. |
| 7,757,700 B2 | 7/2010 | Barnhill et al. |
| 7,758,701 B2 | 7/2010 | Barnhill et al. |
| 7,761,127 B2 | 7/2010 | Al-Ali et al. |
| 7,761,312 B2 | 7/2010 | Brown |
| 7,764,982 B2 | 7/2010 | Dalke et al. |
| 7,765,112 B2 | 7/2010 | Brown |
| D621,516 S | 8/2010 | Kiani et al. |
| 7,766,829 B2 | 8/2010 | Sloan et al. |
| 7,769,605 B2 | 8/2010 | Brown |
| 7,778,845 B2 | 8/2010 | Brown |
| 7,789,095 B2 | 9/2010 | Barnhill et al. |
| 7,791,155 B2 | 9/2010 | Diab |
| 7,796,045 B2 | 9/2010 | Spear et al. |
| 7,801,745 B2 | 9/2010 | Walker et al. |
| 7,809,585 B1 | 10/2010 | Ghouri |
| RE41,912 E | 11/2010 | Parker |
| 7,844,361 B2 | 11/2010 | Jean-Pierre |
| 7,880,626 B2 | 2/2011 | Al-Ali et al. |
| 7,909,772 B2 | 3/2011 | Popov et al. |
| 7,919,713 B2 | 4/2011 | Al-Ali et al. |
| 7,937,128 B2 | 5/2011 | Al-Ali |
| 7,937,129 B2 | 5/2011 | Mason et al. |
| 7,941,199 B2 | 5/2011 | Kiani |
| 7,957,780 B2 | 6/2011 | Lamego et al. |
| 7,962,188 B2 | 6/2011 | Kiani et al. |
| 7,976,472 B2 | 7/2011 | Kiani |
| 7,990,382 B2 | 8/2011 | Kiani |
| 8,008,088 B2 | 8/2011 | Bellott et al. |
| RE42,753 E | 9/2011 | Kiani-Azarbayjany et al. |
| 8,028,701 B2 | 10/2011 | Al-Ali et al. |
| 8,048,040 B2 | 11/2011 | Kiani |
| 8,050,728 B2 | 11/2011 | Al-Ali et al. |
| 8,055,509 B1 | 11/2011 | Walker et al. |
| 8,069,056 B2 | 11/2011 | Walker et al. |
| RE43,169 E | 2/2012 | Parker |
| 8,118,620 B2 | 2/2012 | Al-Ali et al. |
| 8,130,105 B2 | 3/2012 | Al-Ali et al. |
| 8,182,443 B1 | 5/2012 | Kiani |
| 8,190,223 B2 | 5/2012 | Al-Ali et al. |
| 8,203,438 B2 | 6/2012 | Kiani et al. |
| 8,203,704 B2 | 6/2012 | Merritt et al. |
| 8,219,172 B2 | 7/2012 | Schurman et al. |
| 8,224,411 B2 | 7/2012 | Al-Ali et al. |
| 8,229,532 B2 | 7/2012 | Davis |
| 8,233,955 B2 | 7/2012 | Al-Ali et al. |
| 8,255,026 B1 | 8/2012 | Al-Ali |
| 8,265,723 B1 | 9/2012 | McHale et al. |
| 8,274,360 B2 | 9/2012 | Sampath et al. |
| 8,280,473 B2 | 10/2012 | Al-Ali |
| 8,315,683 B2 | 11/2012 | Al-Ali et al. |
| RE43,860 E | 12/2012 | Parker |
| 8,346,330 B2 | 1/2013 | Lamego |
| 8,353,842 B2 | 1/2013 | Al-Ali et al. |
| 8,355,766 B2 | 1/2013 | Macneish, III et al. |
| 8,374,665 B2 | 2/2013 | Lamego |
| 8,388,353 B2 | 3/2013 | Kiani et al. |
| 8,401,602 B2 | 3/2013 | Kiani |
| 8,414,499 B2 | 4/2013 | Al-Ali et al. |
| 8,418,524 B2 | 4/2013 | Al-Ali |
| 8,428,967 B2 | 4/2013 | Olsen et al. |
| 8,430,817 B1 | 4/2013 | Al-Ali et al. |
| 8,437,825 B2 | 5/2013 | Dalvi et al. |
| 8,455,290 B2 | 6/2013 | Siskavich |
| 8,457,707 B2 | 6/2013 | Kiani |
| 8,471,713 B2 | 6/2013 | Poeze et al. |
| 8,473,020 B2 | 6/2013 | Kiani et al. |
| 8,509,867 B2 | 8/2013 | Workman et al. |
| 8,515,509 B2 | 8/2013 | Bruinsma et al. |
| 8,523,781 B2 | 9/2013 | Al-Ali |
| D692,145 S | 10/2013 | Al-Ali et al. |
| 8,571,617 B2 | 10/2013 | Reichgott et al. |
| 8,571,618 B1 | 10/2013 | Lamego et al. |
| 8,571,619 B2 | 10/2013 | Al-Ali et al. |
| 8,577,431 B2 | 11/2013 | Lamego et al. |
| 8,584,345 B2 | 11/2013 | Al-Ali et al. |
| 8,588,880 B2 | 11/2013 | Abdul-Hafiz et al. |
| 8,630,691 B2 | 1/2014 | Lamego et al. |
| 8,641,631 B2 | 2/2014 | Sierra et al. |
| 8,652,060 B2 | 2/2014 | Al-Ali |
| 8,666,468 B1 | 3/2014 | Al-Ali |
| 8,670,811 B2 | 3/2014 | O'Reilly |
| RE44,823 E | 4/2014 | Parker |
| RE44,875 E | 4/2014 | Kiani et al. |
| 8,688,183 B2 | 4/2014 | Bruinsma et al. |
| 8,690,799 B2 | 4/2014 | Telfort et al. |
| 8,702,627 B2 | 4/2014 | Telfort et al. |
| 8,712,494 B1 | 4/2014 | MacNeish, III et al. |
| 8,715,206 B2 | 5/2014 | Telfort et al. |
| 8,723,677 B1 | 5/2014 | Kiani |
| 8,740,792 B1 | 6/2014 | Kiani et al. |
| 8,755,535 B2 | 6/2014 | Telfort et al. |
| 8,755,872 B1 | 6/2014 | Marinow |
| 8,764,671 B2 | 7/2014 | Kiani |
| 8,768,423 B2 | 7/2014 | Shakespeare et al. |
| 8,771,204 B2 | 7/2014 | Telfort et al. |
| 8,781,544 B2 | 7/2014 | Al-Ali et al. |
| 8,790,268 B2 | 7/2014 | Al-Ali |
| 8,801,613 B2 | 8/2014 | Al-Ali et al. |
| 8,821,397 B2 | 9/2014 | Al-Ali et al. |
| 8,821,415 B2 | 9/2014 | Al-Ali et al. |
| 8,830,449 B1 | 9/2014 | Lamego et al. |
| 8,840,549 B2 | 9/2014 | Al-Ali et al. |
| 8,852,094 B2 | 10/2014 | Al-Ali et al. |
| 8,852,994 B2 | 10/2014 | Wojtczuk et al. |
| 8,897,847 B2 | 11/2014 | Al-Ali |
| 8,911,377 B2 | 12/2014 | Al-Ali |
| 8,989,831 B2 | 3/2015 | Al-Ali et al. |
| 8,998,809 B2 | 4/2015 | Kiani |
| 9,066,666 B2 | 6/2015 | Kiani |
| 9,066,680 B1 | 6/2015 | Al-Ali et al. |
| 9,095,316 B2 | 8/2015 | Welch et al. |
| 9,106,038 B2 | 8/2015 | Telfort et al. |
| 9,107,625 B2 | 8/2015 | Telfort et al. |
| 9,131,881 B2 | 9/2015 | Diab et al. |
| 9,138,180 B1 | 9/2015 | Coverston et al. |
| 9,153,112 B1 | 10/2015 | Kiani et al. |
| 9,192,329 B2 | 11/2015 | Al-Ali |
| 9,192,351 B1 | 11/2015 | Telfort et al. |
| 9,195,385 B2 | 11/2015 | Al-Ali et al. |
| 9,211,095 B1 | 12/2015 | Al-Ali |
| 9,218,454 B2 | 12/2015 | Kiani et al. |
| 9,245,668 B1 | 1/2016 | Vo et al. |
| 9,267,572 B2 | 2/2016 | Barker et al. |
| 9,277,880 B2 | 3/2016 | Poeze et al. |
| 9,307,928 B1 | 4/2016 | Al-Ali et al. |
| 9,323,894 B2 | 4/2016 | Kiani |
| D755,392 S | 5/2016 | Hwang et al. |
| 9,326,712 B1 | 5/2016 | Kiani |
| 9,392,945 B2 | 7/2016 | Al-Ali et al. |
| 9,408,542 B1 | 8/2016 | Kinast et al. |
| 9,436,645 B2 | 9/2016 | Al-Ali et al. |
| 9,445,759 B1 | 9/2016 | Lamego et al. |
| 9,474,474 B2 | 10/2016 | Lamego et al. |
| 9,480,435 B2 | 11/2016 | Olsen |
| 9,510,779 B2 | 12/2016 | Poeze et al. |
| 9,517,024 B2 | 12/2016 | Kiani et al. |
| 9,532,722 B2 | 1/2017 | Lamego et al. |
| 9,560,996 B2 | 2/2017 | Kiani |
| 9,579,039 B2 | 2/2017 | Jansen et al. |
| 9,622,692 B2 | 4/2017 | Lamego et al. |
| D788,312 S | 5/2017 | Al-Ali et al. |
| 9,649,054 B2 | 5/2017 | Lamego et al. |
| 9,697,928 B2 | 7/2017 | Al-Ali et al. |
| 9,717,458 B2 | 8/2017 | Lamego et al. |
| 9,724,016 B1 | 8/2017 | Al-Ali et al. |
| 9,724,024 B2 | 8/2017 | Al-Ali |
| 9,724,025 B1 | 8/2017 | Kiani et al. |
| 9,749,232 B2 | 8/2017 | Sampath et al. |
| 9,750,442 B2 | 9/2017 | Olsen |

(56) References Cited

U.S. PATENT DOCUMENTS

| | | |
|---|---|---|
| 9,750,461 B1 | 9/2017 | Telfort |
| 9,775,545 B2 | 10/2017 | Al-Ali et al. |
| 9,778,079 B1 | 10/2017 | Al-Ali et al. |
| 9,782,077 B2 | 10/2017 | Lamego et al. |
| 9,787,568 B2 | 10/2017 | Lamego et al. |
| 9,808,188 B1 | 11/2017 | Perea et al. |
| 9,839,379 B2 | 12/2017 | Al-Ali et al. |
| 9,839,381 B1 | 12/2017 | Weber et al. |
| 9,847,749 B2 | 12/2017 | Kiani et al. |
| 9,848,800 B1 | 12/2017 | Lee et al. |
| 9,861,298 B2 | 1/2018 | Eckerbom et al. |
| 9,861,305 B1 | 1/2018 | Weber et al. |
| 9,877,650 B2 | 1/2018 | Muhsin et al. |
| 9,891,079 B2 | 2/2018 | Dalvi |
| 9,924,897 B1 | 3/2018 | Abdul-Hafiz |
| 9,936,917 B2 | 4/2018 | Poeze et al. |
| 9,955,937 B2 | 5/2018 | Telfort |
| 9,965,946 B2 | 5/2018 | Al-Ali et al. |
| D820,865 S | 6/2018 | Muhsin et al. |
| 9,986,952 B2 | 6/2018 | Dalvi et al. |
| D822,215 S | 7/2018 | Al-Ali et al. |
| D822,216 S | 7/2018 | Barker et al. |
| 10,010,276 B2 | 7/2018 | Al-Ali et al. |
| 10,086,138 B1 | 10/2018 | Novak, Jr. |
| 10,111,591 B2 | 10/2018 | Dyell et al. |
| D833,624 S | 11/2018 | DeJong et al. |
| 10,123,729 B2 | 11/2018 | Dyell et al. |
| D835,282 S | 12/2018 | Barker et al. |
| D835,283 S | 12/2018 | Barker et al. |
| D835,284 S | 12/2018 | Barker et al. |
| D835,285 S | 12/2018 | Barker et al. |
| 10,149,616 B2 | 12/2018 | Al-Ali et al. |
| 10,154,815 B2 | 12/2018 | Al-Ali et al. |
| 10,159,412 B2 | 12/2018 | Lamego et al. |
| 10,188,348 B2 | 1/2019 | Al-Ali et al. |
| RE47,218 E | 2/2019 | Al-Ali |
| RE47,244 E | 2/2019 | Kiani et al. |
| RE47,249 E | 2/2019 | Kiani et al. |
| 10,205,291 B2 | 2/2019 | Scruggs et al. |
| 10,226,187 B2 | 3/2019 | Al-Ali et al. |
| 10,231,657 B2 | 3/2019 | Al-Ali et al. |
| 10,231,670 B2 | 3/2019 | Blank et al. |
| RE47,353 E | 4/2019 | Kiani et al. |
| 10,279,247 B2 | 5/2019 | Kiani |
| 10,292,664 B2 | 5/2019 | Al-Ali |
| 10,299,720 B2 | 5/2019 | Brown et al. |
| 10,327,337 B2 | 6/2019 | Schmidt et al. |
| 10,327,713 B2 | 6/2019 | Barker et al. |
| 10,332,630 B2 | 6/2019 | Al-Ali |
| 10,383,520 B2 | 8/2019 | Wojtczuk et al. |
| 10,383,527 B2 | 8/2019 | Al-Ali |
| 10,388,120 B2 | 8/2019 | Muhsin et al. |
| D864,120 S | 10/2019 | Forrest et al. |
| 10,441,181 B1 | 10/2019 | Telfort et al. |
| 10,441,196 B2 | 10/2019 | Eckerbom et al. |
| 10,448,844 B2 | 10/2019 | Al-Ali et al. |
| 10,448,871 B2 | 10/2019 | Al-Ali et al. |
| 10,456,038 B2 | 10/2019 | Lamego et al. |
| 10,463,340 B2 | 11/2019 | Telfort et al. |
| 10,471,159 B1 | 11/2019 | Lapotko et al. |
| 10,505,311 B2 | 12/2019 | Al-Ali et al. |
| 10,524,738 B2 | 1/2020 | Olsen |
| 10,532,174 B2 | 1/2020 | Al-Ali |
| 10,537,285 B2 | 1/2020 | Shreim et al. |
| 10,542,903 B2 | 1/2020 | Al-Ali et al. |
| 10,555,678 B2 | 2/2020 | Dalvi et al. |
| 10,568,553 B2 | 2/2020 | O'Neil et al. |
| RE47,882 E | 3/2020 | Al-Ali |
| 10,608,817 B2 | 3/2020 | Haider et al. |
| D880,477 S | 4/2020 | Forrest et al. |
| 10,617,302 B2 | 4/2020 | Al-Ali et al. |
| 10,617,335 B2 | 4/2020 | Al-Ali et al. |
| 10,637,181 B2 | 4/2020 | Al-Ali et al. |
| D887,548 S | 6/2020 | Abdul-Hafiz et al. |
| D887,549 S | 6/2020 | Abdul-Hafiz et al. |
| 10,667,764 B2 | 6/2020 | Ahmed et al. |
| D890,708 S | 7/2020 | Forrest et al. |
| 10,721,785 B2 | 7/2020 | Al-Ali |
| 10,736,518 B2 | 8/2020 | Al-Ali et al. |
| 10,750,984 B2 | 8/2020 | Pauley et al. |
| D897,098 S | 9/2020 | Al-Ali |
| 10,779,098 B2 | 9/2020 | Iswanto et al. |
| 10,827,961 B1 | 11/2020 | Iyengar et al. |
| 10,828,007 B1 | 11/2020 | Telfort et al. |
| 10,832,818 B2 | 11/2020 | Muhsin et al. |
| 10,849,554 B2 | 12/2020 | Shreim et al. |
| 10,856,750 B2 | 12/2020 | Indorf et al. |
| D906,970 S | 1/2021 | Forrest et al. |
| 10,918,281 B2 | 2/2021 | Al-Ali et al. |
| 10,932,705 B2 | 3/2021 | Muhsin et al. |
| 10,932,729 B2 | 3/2021 | Kiani et al. |
| 2001/0009398 A1 | 7/2001 | Sekura et al. |
| 2001/0017817 A1 | 8/2001 | de la Huerga |
| 2001/0028308 A1 | 10/2001 | de la Huerga |
| 2001/0034477 A1 | 10/2001 | Mansfield et al. |
| 2001/0039483 A1 | 11/2001 | Brand et al. |
| 2001/0056359 A1 | 12/2001 | Abreu |
| 2002/0010401 A1 | 1/2002 | Bushmakin et al. |
| 2002/0027507 A1 | 3/2002 | Yarin et al. |
| 2002/0058864 A1 | 5/2002 | Mansfield et al. |
| 2002/0067270 A1 | 6/2002 | Yarin et al. |
| 2002/0084904 A1 | 7/2002 | de la Huerga |
| 2002/0093427 A1 | 7/2002 | Roth et al. |
| 2002/0104848 A1 | 8/2002 | Burrows et al. |
| 2002/0116509 A1 | 8/2002 | De La Huerga |
| 2002/0128864 A1 | 9/2002 | Maus et al. |
| 2002/0133080 A1 | 9/2002 | Apruzzese et al. |
| 2002/0143563 A1 | 10/2002 | Hufford et al. |
| 2002/0147526 A1 | 10/2002 | Siegel |
| 2002/0169635 A1 | 11/2002 | Shillingburg |
| 2002/0175903 A1 | 11/2002 | Fahraeus et al. |
| 2003/0013975 A1 | 1/2003 | Kiani |
| 2003/0018243 A1 | 1/2003 | Gerhardt et al. |
| 2003/0037702 A1 * | 2/2003 | Jacobson .............. 106/31.92 |
| 2003/0060286 A1 | 3/2003 | Walker et al. |
| 2003/0063522 A1 | 4/2003 | Sagar |
| 2003/0086338 A1 | 5/2003 | Sastry et al. |
| 2003/0099158 A1 | 5/2003 | De La Huerga |
| 2003/0137258 A1 | 7/2003 | Piepgras et al. |
| 2003/0144582 A1 | 7/2003 | Cohen et al. |
| 2003/0156288 A1 | 8/2003 | Barnum et al. |
| 2003/0212312 A1 | 11/2003 | Coffin, IV et al. |
| 2004/0009700 A1 | 1/2004 | Patel |
| 2004/0106163 A1 | 6/2004 | Workman, Jr. et al. |
| 2004/0133305 A1 | 7/2004 | Jean-Pierre |
| 2004/0192411 A1 | 9/2004 | Shim |
| 2004/0193446 A1 | 9/2004 | Mayer et al. |
| 2004/0266466 A1 | 12/2004 | Zhao et al. |
| 2005/0047114 A1 * | 3/2005 | Harrell .............. B65D 51/248 |
| | | 362/101 |
| 2005/0055276 A1 | 3/2005 | Kiani et al. |
| 2005/0056531 A1 * | 3/2005 | Yu et al. .............. 200/310 |
| 2005/0171634 A1 | 8/2005 | York et al. |
| 2005/0174216 A1 | 8/2005 | Lintell |
| 2005/0187789 A1 | 8/2005 | Hatlestad et al. |
| 2005/0188853 A1 | 9/2005 | Scannell |
| 2005/0201095 A1 | 9/2005 | Brase et al. |
| 2005/0234317 A1 | 10/2005 | Kiani |
| 2005/0285547 A1 | 12/2005 | Piepgras et al. |
| 2006/0022806 A1 | 2/2006 | Auerbach |
| 2006/0073719 A1 | 4/2006 | Kiani |
| 2006/0124655 A1 | 6/2006 | Ratnakar |
| 2006/0139150 A1 | 6/2006 | Brue |
| 2006/0154642 A1 | 7/2006 | Scannell |
| 2006/0189871 A1 | 8/2006 | Al-Ali et al. |
| 2006/0218014 A1 | 9/2006 | Walker et al. |
| 2006/0218015 A1 | 9/2006 | Walker et al. |
| 2006/0231109 A1 | 10/2006 | Howell et al. |
| 2006/0241355 A1 | 10/2006 | Howell et al. |
| 2007/0016443 A1 | 1/2007 | Wachman et al. |
| 2007/0016447 A1 | 1/2007 | Brown |
| 2007/0073116 A1 | 3/2007 | Kiani et al. |
| 2007/0073560 A1 | 3/2007 | Walker et al. |
| 2007/0138195 A1 | 6/2007 | Anderson et al. |

(56) References Cited

U.S. PATENT DOCUMENTS

| | | |
|---|---|---|
| 2007/0180140 A1 | 8/2007 | Welch et al. |
| 2007/0194890 A1 | 8/2007 | Brue |
| 2007/0195526 A1 | 8/2007 | Dowling et al. |
| 2007/0206375 A1 | 9/2007 | Piepgras et al. |
| 2007/0244377 A1 | 10/2007 | Cozad et al. |
| 2008/0001737 A1 | 1/2008 | Metry |
| 2008/0064965 A1 | 3/2008 | Jay et al. |
| 2008/0094228 A1 | 4/2008 | Welch et al. |
| 2008/0114490 A1 | 5/2008 | Jean-Pierre |
| 2008/0142472 A1 | 6/2008 | Metry et al. |
| 2008/0154099 A1 | 6/2008 | Aspel et al. |
| 2008/0169910 A1 | 7/2008 | Greene et al. |
| 2008/0221418 A1 | 9/2008 | Al-Ali et al. |
| 2008/0284716 A1 | 11/2008 | Edwards et al. |
| 2009/0036759 A1 | 2/2009 | Ault et al. |
| 2009/0051560 A1* | 2/2009 | Manning et al. .......... 340/691.6 |
| 2009/0093687 A1 | 4/2009 | Telfort et al. |
| 2009/0095926 A1 | 4/2009 | MacNeish, III |
| 2009/0134181 A1 | 5/2009 | Wachman et al. |
| 2009/0247984 A1 | 10/2009 | Lamego et al. |
| 2009/0259495 A1 | 10/2009 | Rosenfeld |
| 2009/0294521 A1 | 12/2009 | De La Huerga |
| 2010/0004518 A1 | 1/2010 | Vo et al. |
| 2010/0030040 A1 | 2/2010 | Poeze et al. |
| 2010/0063840 A1 | 3/2010 | Hoyme et al. |
| 2010/0099964 A1 | 4/2010 | O'Reilly et al. |
| 2010/0234718 A1 | 9/2010 | Sampath et al. |
| 2010/0328099 A1 | 12/2010 | Wachman et al. |
| 2011/0028806 A1 | 2/2011 | Merritt et al. |
| 2011/0028809 A1 | 2/2011 | Goodman |
| 2011/0040197 A1 | 2/2011 | Welch et al. |
| 2011/0082711 A1 | 4/2011 | Poeze et al. |
| 2011/0087081 A1 | 4/2011 | Kiani et al. |
| 2011/0118561 A1 | 5/2011 | Tari et al. |
| 2011/0137297 A1 | 6/2011 | Kiani et al. |
| 2011/0172498 A1 | 7/2011 | Olsen et al. |
| 2011/0230733 A1 | 9/2011 | Al-Ali |
| 2012/0123231 A1 | 5/2012 | O'Reilly |
| 2012/0150677 A1 | 6/2012 | Shuster |
| 2012/0165629 A1 | 6/2012 | Merritt et al. |
| 2012/0209084 A1 | 8/2012 | Olsen et al. |
| 2012/0226117 A1 | 9/2012 | Lamego et al. |
| 2012/0278454 A1 | 11/2012 | Stewart et al. |
| 2012/0283524 A1 | 11/2012 | Kiani et al. |
| 2013/0023775 A1 | 1/2013 | Lamego et al. |
| 2013/0041591 A1 | 2/2013 | Lamego |
| 2013/0060147 A1 | 3/2013 | Welch et al. |
| 2013/0096405 A1 | 4/2013 | Garfio |
| 2013/0296672 A1 | 11/2013 | O'Neil et al. |
| 2013/0345921 A1 | 12/2013 | Al-Ali et al. |
| 2014/0166076 A1 | 6/2014 | Kiani et al. |
| 2014/0180160 A1 | 6/2014 | Brown et al. |
| 2014/0187973 A1 | 7/2014 | Brown et al. |
| 2014/0275871 A1 | 9/2014 | Lamego et al. |
| 2014/0275872 A1 | 9/2014 | Merritt et al. |
| 2014/0303989 A1 | 10/2014 | Ferguson |
| 2014/0316217 A1 | 10/2014 | Purdon et al. |
| 2014/0316218 A1 | 10/2014 | Purdon et al. |
| 2014/0323897 A1 | 10/2014 | Brown et al. |
| 2014/0323898 A1 | 10/2014 | Purdon et al. |
| 2015/0005600 A1 | 1/2015 | Blank et al. |
| 2015/0011907 A1 | 1/2015 | Purdon et al. |
| 2015/0073241 A1 | 3/2015 | Lamego |
| 2015/0080754 A1 | 3/2015 | Purdon et al. |
| 2015/0099950 A1 | 4/2015 | Al-Ali et al. |
| 2015/0106228 A1 | 4/2015 | Shuster |
| 2015/0106238 A1 | 4/2015 | Shuster |
| 2016/0196388 A1 | 7/2016 | Lamego |
| 2016/0367173 A1 | 12/2016 | Dalvi et al. |
| 2017/0024748 A1 | 1/2017 | Haider |
| 2017/0042488 A1 | 2/2017 | Muhsin |
| 2017/0173632 A1 | 6/2017 | Al-Ali |
| 2017/0251974 A1 | 9/2017 | Shreim et al. |
| 2017/0311891 A1 | 11/2017 | Kiani et al. |
| 2018/0103874 A1 | 4/2018 | Lee et al. |
| 2018/0242926 A1 | 8/2018 | Muhsin et al. |
| 2018/0247353 A1 | 8/2018 | Al-Ali et al. |
| 2018/0247368 A1 | 8/2018 | Shuster |
| 2018/0247712 A1 | 8/2018 | Muhsin et al. |
| 2018/0256087 A1 | 9/2018 | Al-Ali et al. |
| 2018/0300919 A1 | 10/2018 | Muhsin et al. |
| 2018/0310822 A1 | 11/2018 | Indorf et al. |
| 2018/0310823 A1 | 11/2018 | Al-Ali et al. |
| 2018/0317826 A1 | 11/2018 | Muhsin et al. |
| 2019/0015023 A1 | 1/2019 | Monfre |
| 2019/0117070 A1 | 4/2019 | Muhsin et al. |
| 2019/0200941 A1 | 7/2019 | Chandran et al. |
| 2019/0239787 A1 | 8/2019 | Pauley et al. |
| 2019/0320906 A1 | 10/2019 | Olsen |
| 2019/0374139 A1 | 12/2019 | Kiani et al. |
| 2019/0374173 A1 | 12/2019 | Kiani et al. |
| 2019/0374713 A1 | 12/2019 | Kiani et al. |
| 2020/0060869 A1 | 2/2020 | Telfort et al. |
| 2020/0111552 A1 | 4/2020 | Ahmed |
| 2020/0113435 A1 | 4/2020 | Muhsin |
| 2020/0113488 A1 | 4/2020 | Al-Ali et al. |
| 2020/0113496 A1 | 4/2020 | Scruggs et al. |
| 2020/0113497 A1 | 4/2020 | Triman et al. |
| 2020/0113520 A1 | 4/2020 | Abdul-Hafiz et al. |
| 2020/0138288 A1 | 5/2020 | Al-Ali et al. |
| 2020/0138368 A1 | 5/2020 | Kiani et al. |
| 2020/0163597 A1 | 5/2020 | Dalvi et al. |
| 2020/0196877 A1 | 6/2020 | Vo et al. |
| 2020/0253474 A1 | 8/2020 | Muhsin et al. |
| 2020/0253544 A1 | 8/2020 | Belur Nagaraj et al. |
| 2020/0275841 A1 | 9/2020 | Telfort et al. |
| 2020/0288983 A1 | 9/2020 | Telfort et al. |
| 2020/0321793 A1 | 10/2020 | Al-Ali et al. |
| 2020/0329983 A1 | 10/2020 | Al-Ali et al. |
| 2020/0329984 A1 | 10/2020 | Al-Ali et al. |
| 2020/0329993 A1 | 10/2020 | Al-Ali et al. |
| 2020/0330037 A1 | 10/2020 | Al-Ali et al. |
| 2021/0022628 A1 | 1/2021 | Telfort et al. |

FOREIGN PATENT DOCUMENTS

| | | |
|---|---|---|
| EP | 0 526 166 A2 | 2/1993 |
| WO | WO 95/09386 | 4/1995 |
| WO | WO 95/26009 | 9/1995 |
| WO | WO 00/32097 | 6/2000 |

OTHER PUBLICATIONS

E-Pill, "Pill Vial Multi Alarm featured in Readers Digest," http://www.epill.com/bottle.html, Downloaded Apr. 17, 2010 [3 pgs.].

E-Pill, Beep 'n Tell, http://www.epill.com/beeptell.html, Downloaded Apr. 17, 2010 [7 pgs.].

E-Pill, Catalog, 2010, downloaded from www.epill.com, 2010 [6 pgs.].

Restriction Requirement in U.S. Appl. No. 11/480,859 dated Dec. 22, 2010.

Non-Final Office Action in U.S. Appl. No. 11/480,859 dated Aug. 5, 2011.

Final Office Action in U.S. Appl. No. 11/480,859 dated Mar. 30, 2012.

Non-Final Office Action in U.S. Appl. No. 11/480,859 dated Sep. 24, 2014.

Non-Final Office Action in U.S. Appl. No. 11/480,859 dated Feb. 6, 2015.

Non-Final Office Action in U.S. Appl. No. 12/352,647 dated Mar. 24, 2011.

Final Office Action in U.S. Appl. No. 12/352,647 dated Aug. 22, 2011.

Advisory Action in U.S. Appl. No. 12/352,647 dated Nov. 16, 2011.

Non-Final Office Action in U.S. Appl. No. 12/352,647 dated Nov. 28, 2012.

Non-Final Office Action in U.S. Appl. No. 12/854,398 dated Mar. 31, 2011.

Final Office Action in U.S. Appl. No. 12/854,398 dated Oct. 11, 2011.

(56) References Cited

OTHER PUBLICATIONS

Non-Final Office Action in U.S. Appl. No. 12/854,398 dated Sep. 9, 2014.
Non-Final Office Action in U.S. Appl. No. 12/854,398 dated Mar. 26, 2015.
Notice of Allowance in U.S. Appl. No. 29/299,853 dated Feb. 2, 2009.

* cited by examiner

© 2010 Vitality, Inc.

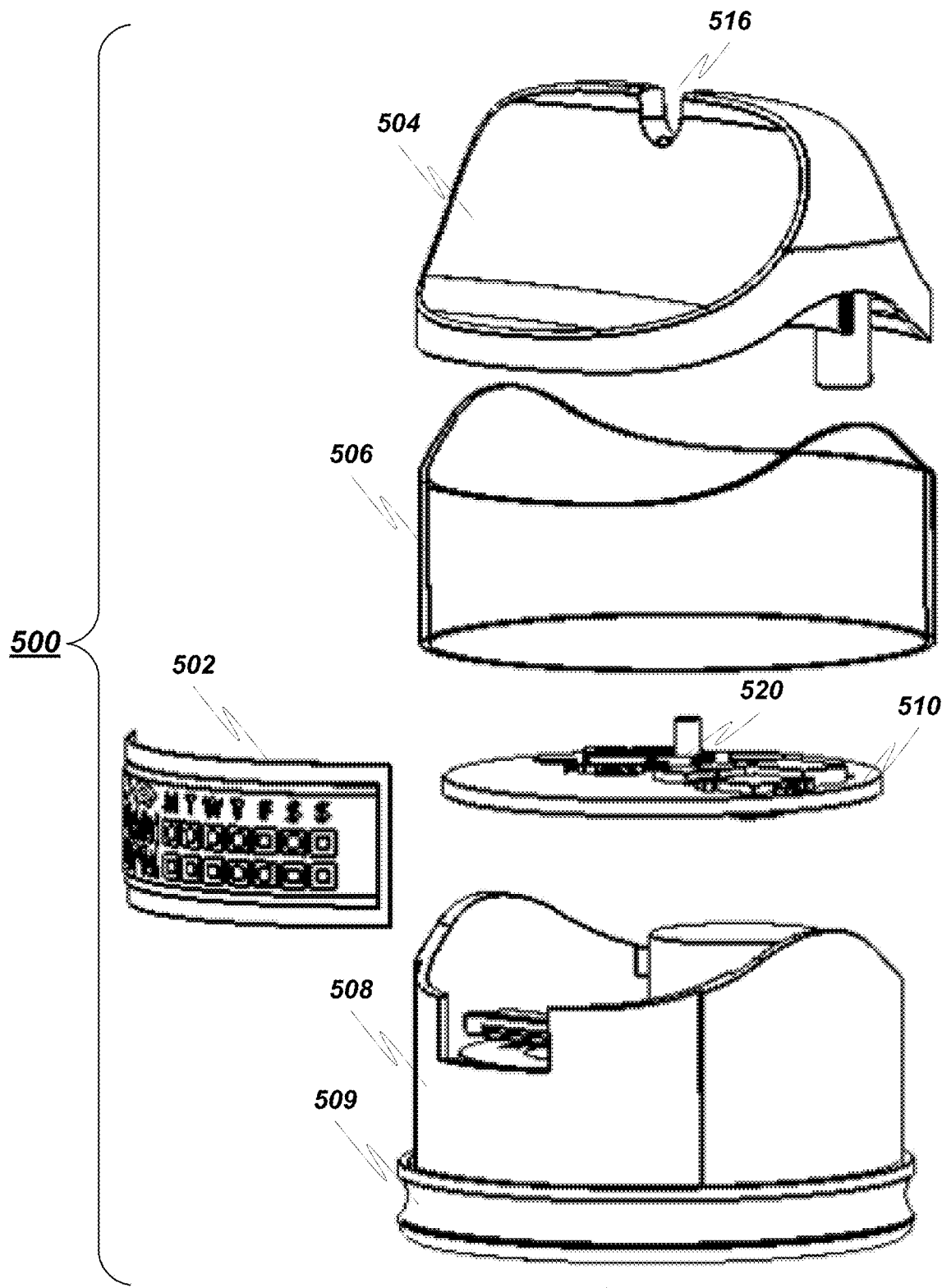
Fig. 4A  © 2010 Vitality, Inc.

© 2010 Vitality, Inc.

© 2010 Vitality, Inc.

MEDICINE BOTTLE CAP WITH ELECTRONIC EMBEDDED CURVED DISPLAY

RELATED APPLICATIONS

This application is related to and claims priority from U.S. Provisional Application No. 61/174,045, filed Apr. 30, 2009, titled "Medicine bottle cap with an embedded curved display," the entire contents of which are hereby fully incorporated herein by reference for all purposes.

This application is also related to and also claims priority from co-pending U.S. patent application Ser. No. 11/480,859, filed Jul. 6, 2006, titled "Medication Compliance Systems, methods and devices with configurable and adaptable escalation engine," which claimed priority from U.S. Provisional Application No. 60/698,792, entitled "Medication Compliance platform with intelligent networked pillbox, escalation engine and data signaling feedback loops," filed Jul. 13, 2005, the entire contents of both of which are hereby fully incorporated herein by reference for all purposes.

This application is also related to and also claims priority from co-pending U.S. patent application Ser. No. 12/352,647, filed Jan. 13, 2009, and titled "Medication Dispenser with Automatic Refill," the entire contents of which are hereby fully incorporated herein by reference for all purposes. Application Ser. No. 12/352,647 is a CIP of application Ser. No. 11/480,859, and also claims priority from Application No. 60/698,792.

COPYRIGHT NOTICE

A portion of the disclosure of this patent document contains material which is subject to copyright protection. The copyright owner has no objection to the facsimile reproduction by anyone of the patent document or the patent disclosure, as it appears in the Patent and Trademark Office patent file or records, but otherwise reserves all copyright rights whatsoever.

FIELD OF THE DISCLOSURE

This invention relates to medication compliance, and, more particularly, to methods and devices supporting medication compliance.

INTRODUCTION & BACKGROUND

Medication non-compliance is a major problem in healthcare.

Physicians prescribe medications for a large class of chronic, asymptomatic diseases. These medications must typically be taken daily for the rest of the patient's life in order to sustain quality of life and reduce health risks. Classic examples of diseases in this class include hypertension, hypercholesterolemia and osteoporosis. With many such diseases, a patient feels no different, whether or not they take their medication. So, unlike brushing one's teeth or even exercising, there are no apparent short to medium term costs for non-compliance. This presents a challenge even for those patients who want to comply, let alone those who need a helping hand.

Various attempts have been made in the past to try to increase and improve compliance by patients. Almost all of these systems are essentially reminder systems. For example, there are a large number of pillbox systems that marry alarm clocks to medication containers to remind patients when it is time to take their medication.

While various systems/devices are described here, we do not admit that any of them qualify as prior art to our invention.

There are some compliance intervention systems offered by health care providers designed to remind the patient and alert a remote caregiver. These include a sensor/reminders in the home, a network connection (typically dial-up) to a backend server and outbound messaging/reporting to a caregiver or even back to the patient. These systems, however, are focused on reminding only and while they may include a remote non-professional caregiver in the reminder loop, forgetfulness is only part of the problem.

Other systems try to help patients manage complex medicine regimens. For example, the MD2 device by Interactive Medical Developments of Aurora Healthcare is a coffee maker sized device that stores and dispenses pills like a common gumball machine The MD2 offers prerecorded audio messages to the patient and network connectivity back to a monitoring service. The MD2 is not designed to be portable, to be wirelessly connected to a network, to relay visual queues to another device resident in the home, or trigger escalating feedback to the patient. The focus on the MD2 is to arm disease management companies to assist patients on multiple medications and to help them effectively manage their regimen from home.

MedPartner of Honeywell Hommed is a platform that helps patients manage complex medicine regimes. The MedPartner platform accommodates several pill bottles and alerts the patient when pills in their regimen needs be taken. The MedPartner system uses RFID technology to label the bottle and its location in an egg-crate like base station. It is networked to a healthcare provider's monitoring station (say in home care or nursing home environments).

SimPill of South Africa describes a pill bottle employing a GSM transmitter which reports to a cellular network whenever a pill is taken. They advertise that their system includes a "pill bottle which, when opened, delivers an SMS [short message service] text message to a central server. The SMS contains a unique pillbox ID number as well as some information about the battery status of the pillbox. Each SMS is time stamped. The central server receives the incoming SMS and, if it is within the time tolerances set for the pillbox sending the message is simply stored for statistical purposes. Should no message be received within the time tolerances then the server can be set to produce a number of responses (e.g. sending a text message reminder to the patient's handset, sending a text message prompt to a family member or community based care giver, prompting them to visit the patient to ascertain the cause of non-compliance and provide assistance, sending a text message to a clinic based health professional or any other user determined response), or indeed escalate through these responses as time elapses with no incoming message in response to the previous outgoing message. Data on levels of compliance as measured by the device are stored for future analysis and use." The SimPill device is ultimately another reminder system, based on its developer's theory (expounded on their website), that "[a]n important proportion of non-compliance is caused by the patient simply forgetting to take their medication." When a patient does not take her medication, SimPill reminds the patient and then, possibly, a caregiver. Like the other reminder/alarm systems, SimPill ignores the more complex nature of non-compliance.

A category of medication compliance platforms has been developed specifically for the clinical trial market. In this market it is critically important to capture the dosing data of patients in order to measure their use and the medications efficacy during a clinical research trial. The price point of these devices is necessarily higher and they are built almost as a medical device to suit the stringent requirements of pharmaceutical manufacturers' clinical research requirements. For example, Informedix of Rockville, Md. has a suite of products focused on compliance systems for the clinical trial market. Their Med-eMonitor is designed to be a clinical data capture diary and medication dispensing device in one. It has electronically monitored medication compartments and an instructional text screen. The device requires a cradle to upload the data and receive power. In the Med-eMonitor if the patient does not return the device to the base station there is no local or remote escalations to remind the patient to take their medication. The platform does not know if the device is even in the home. This suite of devices is designed for monolithic deployment—pharmaceutical companies deploy them in a research trial with a strict protocol that each subject patient must use to fulfill the requirements of the study.

Aardex (Aardex, Ltd. and associated company Aprex Corporation), a Swiss company offers a smart cap to fit standard vials for clinical trial dose recording. The AARDEX MEMS (Medication Event Monitoring System) product employs inductive and capacitive wireless uploading technologies that require close proximity to a networked base-station in the patient's home to upload to a personal computer or even a remotely networked back-end database. The device includes an LCD (liquid crystal display). In order to upload the data from the monitoring caps, a patient has to place it on back into a specially designed base station.

Some prior systems, e.g., as shown in U.S. Pat. No. 6,771,174, require a local computer system at each patient's home to monitor the patient's drug taking. The computer can contact a pharmacist or emergency services if the patient deviates from his or her model behavior. Such systems impose heavy cost requirements—a dedicated computer—at each patient's home. In addition, such systems cannot take advantage of information about other patients, in particular, how other patients have responded to various alert schemes. The inventors were the first to realize that it is desirable and useful to apply techniques to a patient that have been learned from other patients.

U.S. Pat. No. 7,081,807 to Lai discloses an electronic pill reminder device that that is retrofitted inside a regular conventional pill bottle cap—installed inside the conventional pill bottle between the bottle cap and the bottle container. When a user closes the pill bottle cap on the bottle container, an electronic timer, with a factory predetermined time interval, is activated. The timer generates alert signals to remind a user that a last pill has been taken and to remind the user to take his next dose.

The present invention improves on prior systems and overcomes their deficiencies.

BRIEF DESCRIPTION OF THE DRAWINGS

The following description, given with respect to the attached drawings, may be better understood with reference to the non-limiting examples of the drawings, wherein:

FIGS. 4A-4E are partially exploded views of the medicine bottle cap with an electronic embedded curved display;

THE PRESENTLY PREFERRED EXEMPLARY EMBODIMENTS OVERVIEW

Well-established behavioral medicine research shows that non-compliance with a medication regimen is fundamentally a behavioral psychology problem. The inventors have realized that timely intervention(s) by machine or human may influence the patient and should increase medication adherence rates.

There are several reasons why patients may not comply with their medication regimens. No one reason or set of reasons may apply to all people. People are motivated in different ways and by different things, and it is an unknown and possibly unique mix of factors that will motivate any particular individual to comply. The inventors have realized that any system for creating or supporting medication compliance will preferably be multi-faceted and be able to learn and adapt to each patient during their course of treatment.

Commonly acknowledged reasons for non-compliance include the following:
  Lack of doctor-patient accountability
  Medication is too expensive
  Lack of social support.
  Patient's complain or perceive difficulty obtaining refills
  Some patients think that they do not need the medication
  Some patients do not know how to use the medication
  Patients forget to take their medication
  Patients complain of unpleasant side effects The inventors have realized that a solution to the lack of compliance problem should deal with some or all of these factors.

System Architecture

Figure 1A:
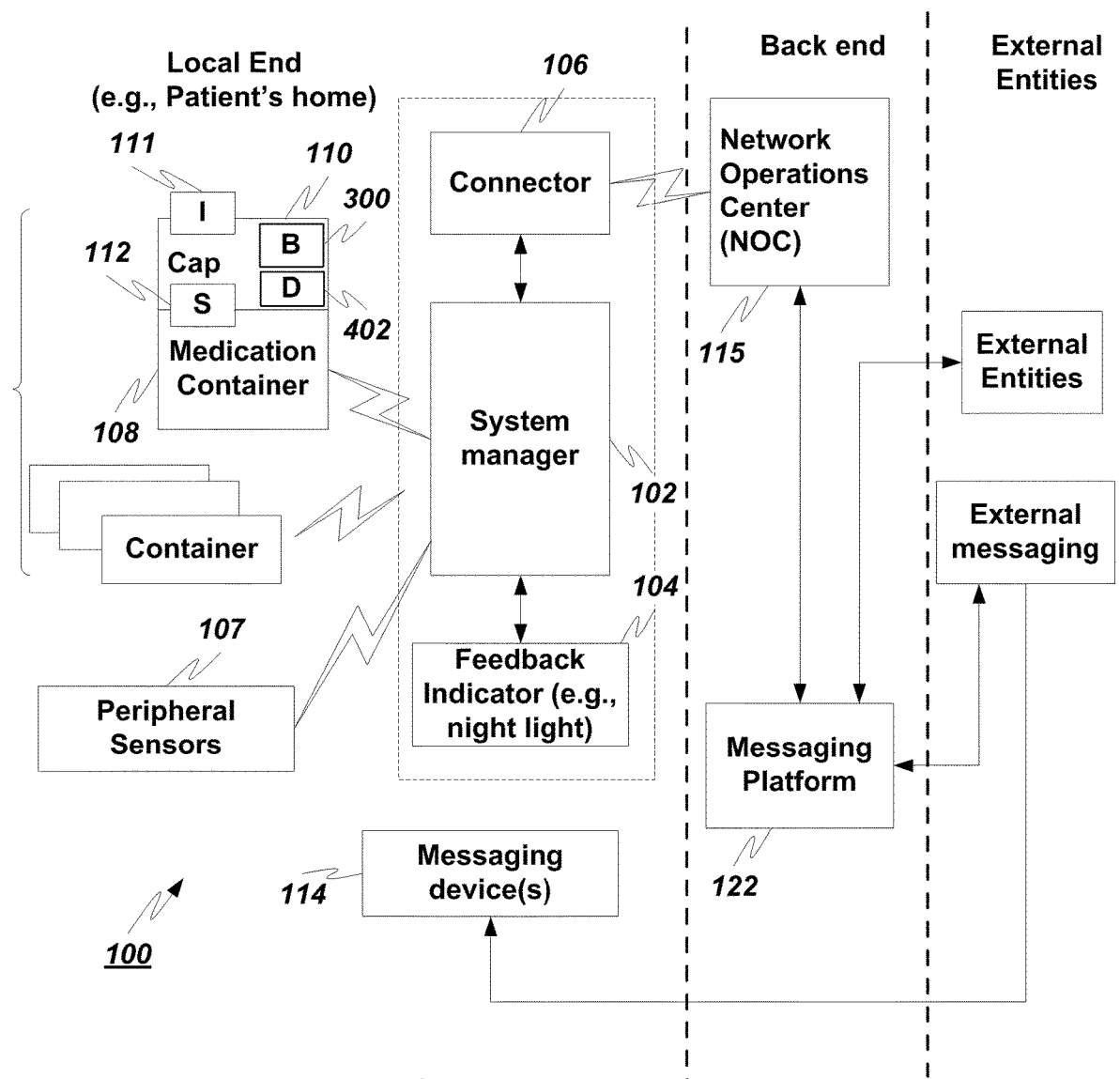
FIG. 1A is an overview of a medication compliance system/framework.
Figure 1B:
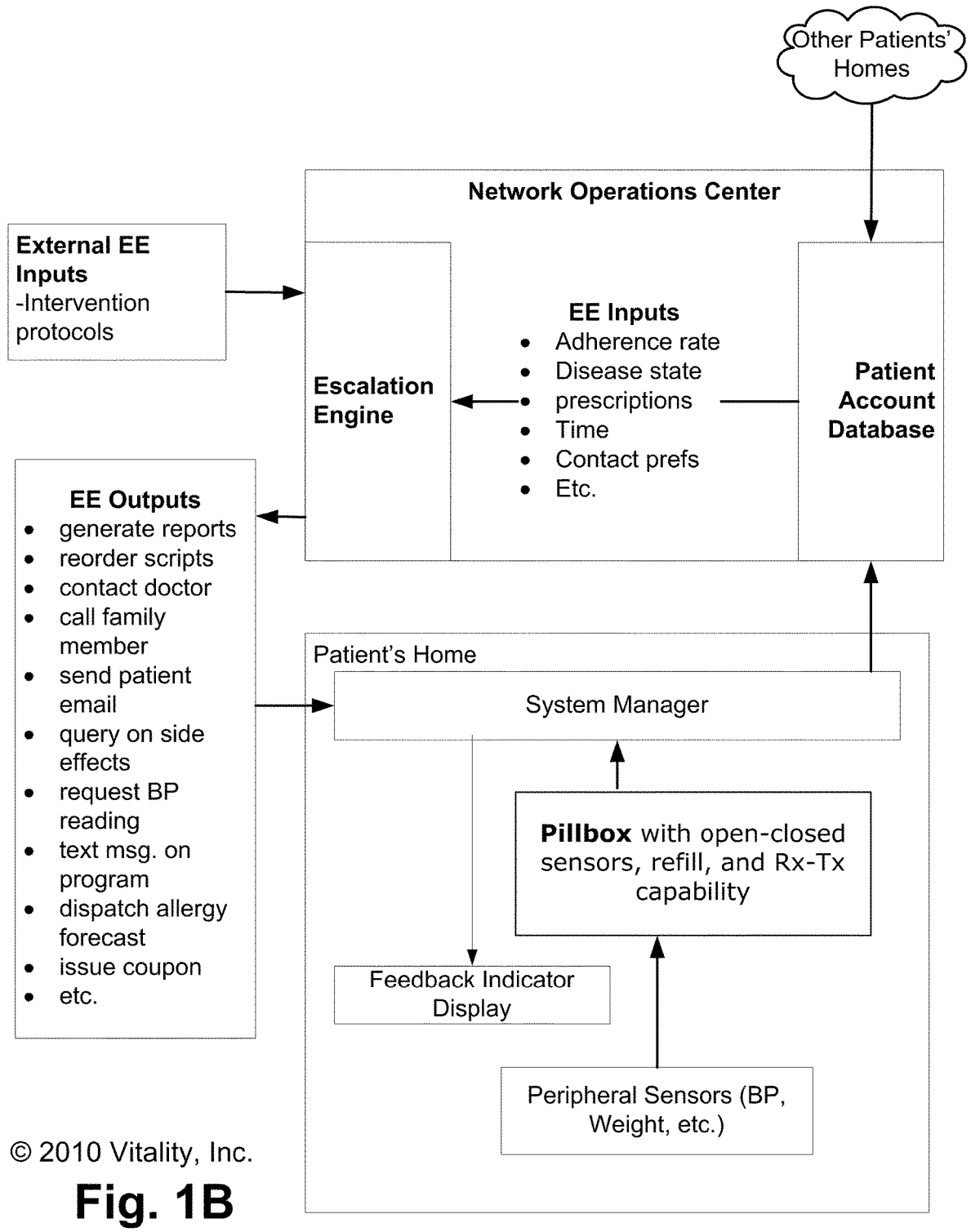
FIG. 1B is a logical overview of the medication compliance framework.

FIG. 1A shows an exemplary medication compliance system/framework 100, and FIG. 1B is a logical overview of the framework. For the purpose of this description, users of the system whose compliance is being monitored and affected are referred to as patients. The use of the word "patient" or "patients" in this description is not meant to limit the scope of the invention or to require any kind of doctor/patient relationship or any other kind of medical or legal relationship with the end users.

A compliance framework can be considered in three logical parts, namely the patients' homes (each a so-called "local end"), a back end, and a part corresponding to external entities that may be involved in the compliance system. The term "patient's home" is used herein to refer to the place (or places) at which a patient is expected to take his medication. It may include, e.g., the patient's home and/or place of work. The patient's home is sometimes referred to herein as the local end.

At a patient's home (or wherever they are supposed to take their medication), the patient is provided with a local system that includes a system manager 102, an optional feedback indicator 104 and a connector 106. The connector 106 allows the local end to connect with the rest of the system (e.g., the back end), and may be a modem, a network connection and the like. Some or all of these components may be integrated into a single device. For example, the system manager 102, a feedback indicator 104, and the connector 106 may be co-located and/or provided in a single device. Alternatively, e.g., the system manager 102 and connector may be formed in a single device. If there is more than one feedback indicator, the system manager may be incorporated into one of them. In a presently preferred embodiment, the system manager 102, feedback indicator 104, and connector 106 are integrated in a single device which includes a "night light" indicator.

The patient's medication is provided in a container 108 with a cap 110. The container 108 may be a regular container or may be specifically adapted to operate with the cap 110. The container/cap combination may be in the form of pill cap, a multi-compartment pillbox, a salve-tube cap, a syringe, an inhaler, a pump dispenser, a drop dispenser and the like. Those of skill in the art will understand, upon reading this description, that the container/cap combination can be used with any medication delivery system and with any type of medication, regardless of its form or dosage. The cap 110 may be fully or partially removable or fully or partially openable, or it may be an integral part of the container through which medication is dispensed. In presently preferred implementations using the cap with the electronic embedded curved display described herein, the container is a regular threaded pill bottle.

At least one sensor 112 is embedded into the medication container 108 and/or the cap 110. The sensor 112 is triggered whenever the container is opened and closed. The sensor may be a pressure sensor, a piezoelectronic sensor, a light sensor, a motion sensor or the like. If more than one sensor is used, the sensors need not all be of the same kind. The function of the sensor(s) is to detect that the medication container has been opened (and then closed). Any sensor(s) (alone or in combination) that achieve this function are acceptable.

Those of skill in the art will realize, upon reading this description, that the container/cap combination may take any form, as long as the system can detect when medication was likely or possibly dispensed.

Although only one medication container 108 is shown in detail in FIG. 1A (for the purposes of this description), it will be understood and appreciated that a patient may have a number of such containers for different medications. Additionally, a particular home (or location) may have medication containers for more than one patient.

A particular system may be open or closed. A closed system will only allow specific and dedicated caps to upload data through the network gateway. (The inventors characterize a closed system as a family of devices in which family members can talk to other family members.) An open system allows all caps to upload their data through the network gateway. (In an open system any member of one family can talk to members of another family.)

Thus, a particular patient may have more than one container (as shown in FIG. 1A), each of which may have a cap and sensors as described above. Those skilled in the art will realize and understand, upon reading this description, that the number and type of containers will depend on the various medications that the particular patient is supposed to take, and that the containers need not all be the same size or type. E.g., some may contain pills; others may contain drops, and so on.

The system assumes that if the medicine container has been opened and then closed, that the medication was actually taken and that the dosage was correct. Preferably the number of pills has to be accounted for upon setup. This known number at the start is decremented by the dosage amount when the cap is opened, and is used to determine whether to initiate a refill.

A local end may also include one or more peripheral sensors 107 to measure and provide data such as the patient's weight, blood pressure (BP), pulse, etc. Peripheral measurements can be provided automatically to the system manager 102 and, in some cases, may be requested by the system manager.

The various containers, sensors and feedback indicators may communicate with the system manager 102 in any known way. The presently preferred implementation uses radio frequencies (ISM band) similar to that used in domestic garage door openers or key fob key-less entry systems. Other protocols such as Bluetooth, ZigBee, Z-wave, 802.11, etc. may be used.

The system manager 102 receives information from and about the sensors in its jurisdiction—the patient's home (in a closed system the system manager will only interact with known sensors). The system manager 102 also communicates with the back end, e.g., via connector 106 using, e.g., a network or a phone system. In some embodiments, the connector 106 is a dedicated telephone dial-up, Ethernet or cellular modem called a network gateway. A network agnostic model may also be used where the network gateway has a plurality of embedded modems and, in the limiting case, the one with the lowest cost of connection, strongest signal or present availability (for instance) defines the connection used. The choice of connection is managed by the central processor or dedicated processor that is in receipt of decision making information from the network(s).

A network gateway is a device that connects the system manager 102 to an external network via POTS (Plain Old Telephone Service) line modem, cellular, pager, 802.11 connections, or the like. In the POTS line modem version, the connector device may be embedded into a so-called "dongle". In addition to the network connectivity, the dongle may communicate with the system manager over wireless, radio frequency communications.

In a presently preferred embodiment, the connector 106 is a cellular modem that connects to the back end via a cellular telephone network.

The suite of devices described above communicates locally (in the home) and asynchronously from the virtual "backend" system components. Schematically these are local devices that communicate with the backend.

Backend

The backend is a data service platform that manages individual patients' data. The structure and operation of the backend are described in detail in co-pending U.S. application Ser. No. 12/352,647, filed Jan. 13, 2009, and titled "Medication Dispenser with Automatic Refill," which has been incorporated herein by reference for all purposes.

Pill Cap

Figure 1C:
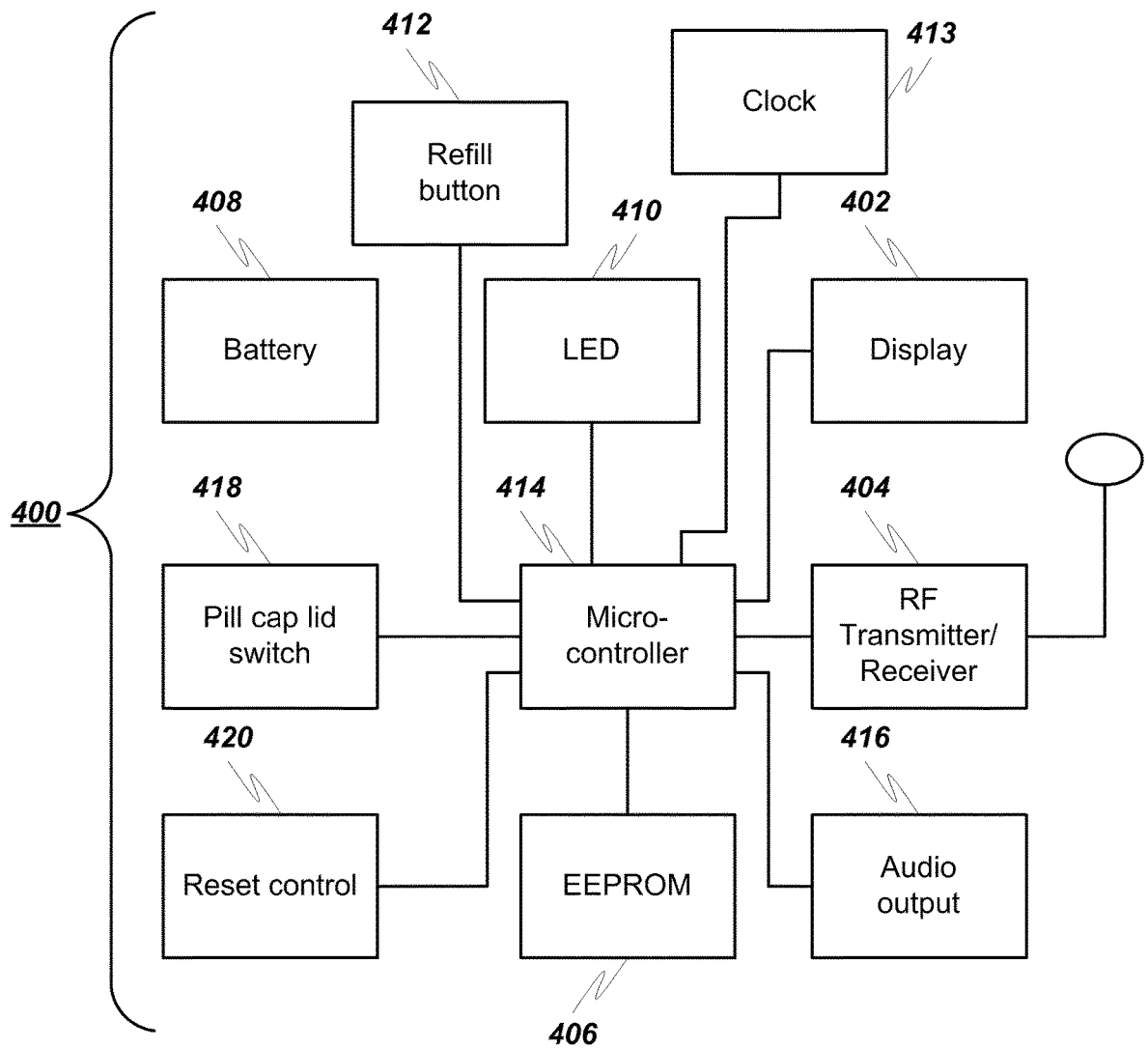
FIG. 1C is a logical diagram showing exemplary internal details of a bottle cap with an electronic embedded curved display.
Figure 2A:
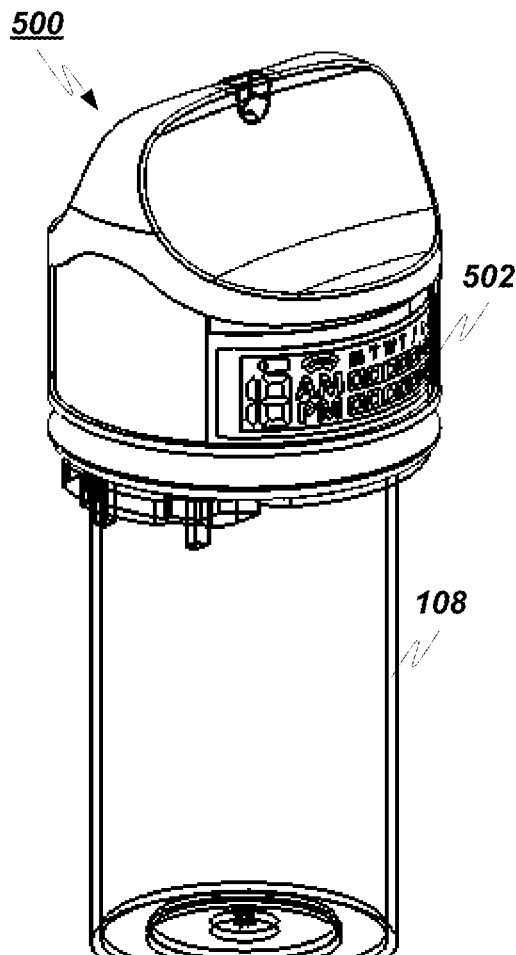
FIGS. 2A-2G show various views of medication containers using a medicine bottle cap with electronic embedded curved display.
Figure 2B:
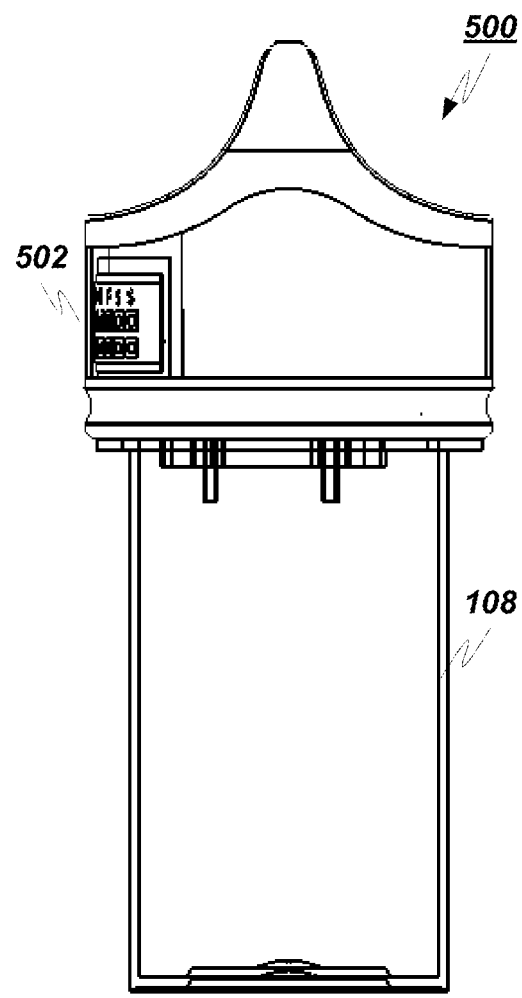
Figure 2C:
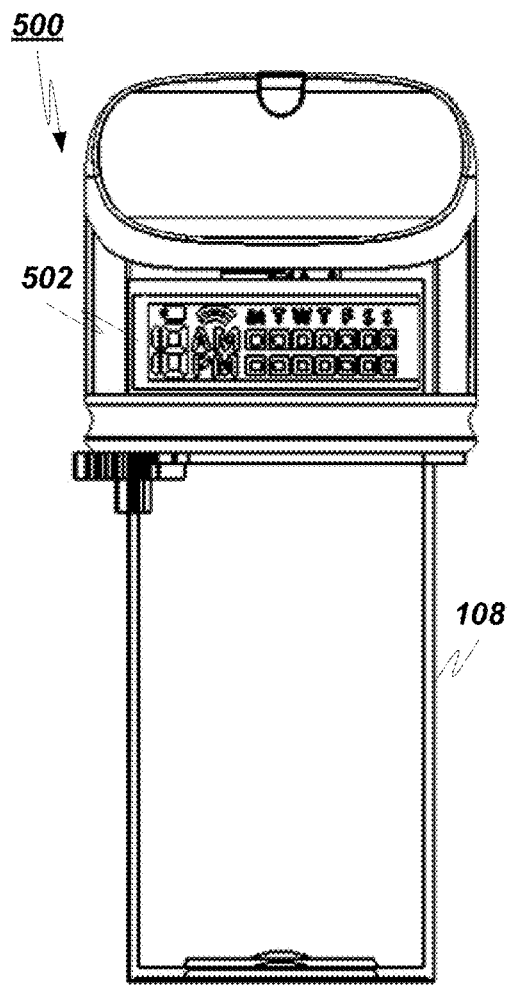
Figure 2D:
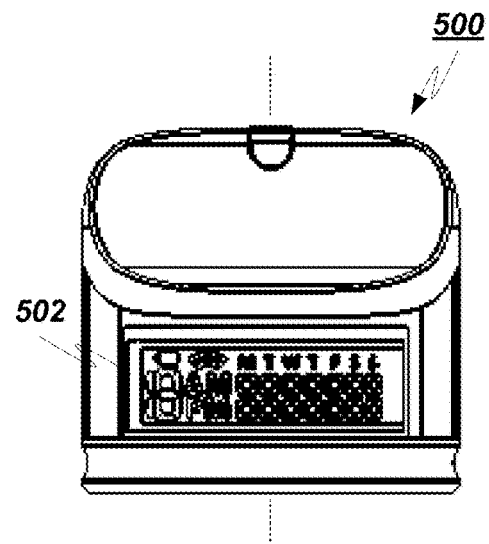
Figure 2D:
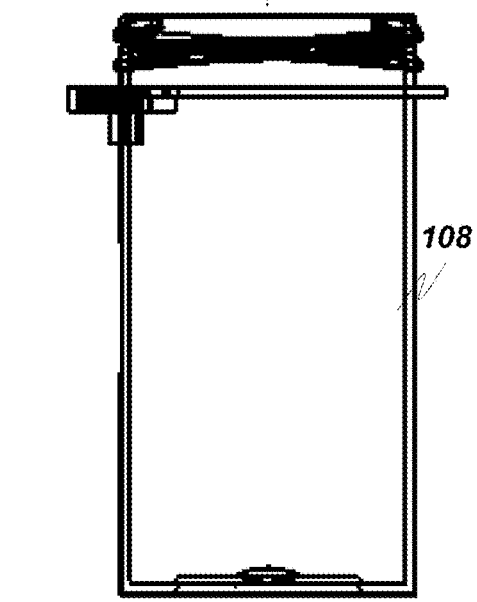
Figure 2E:
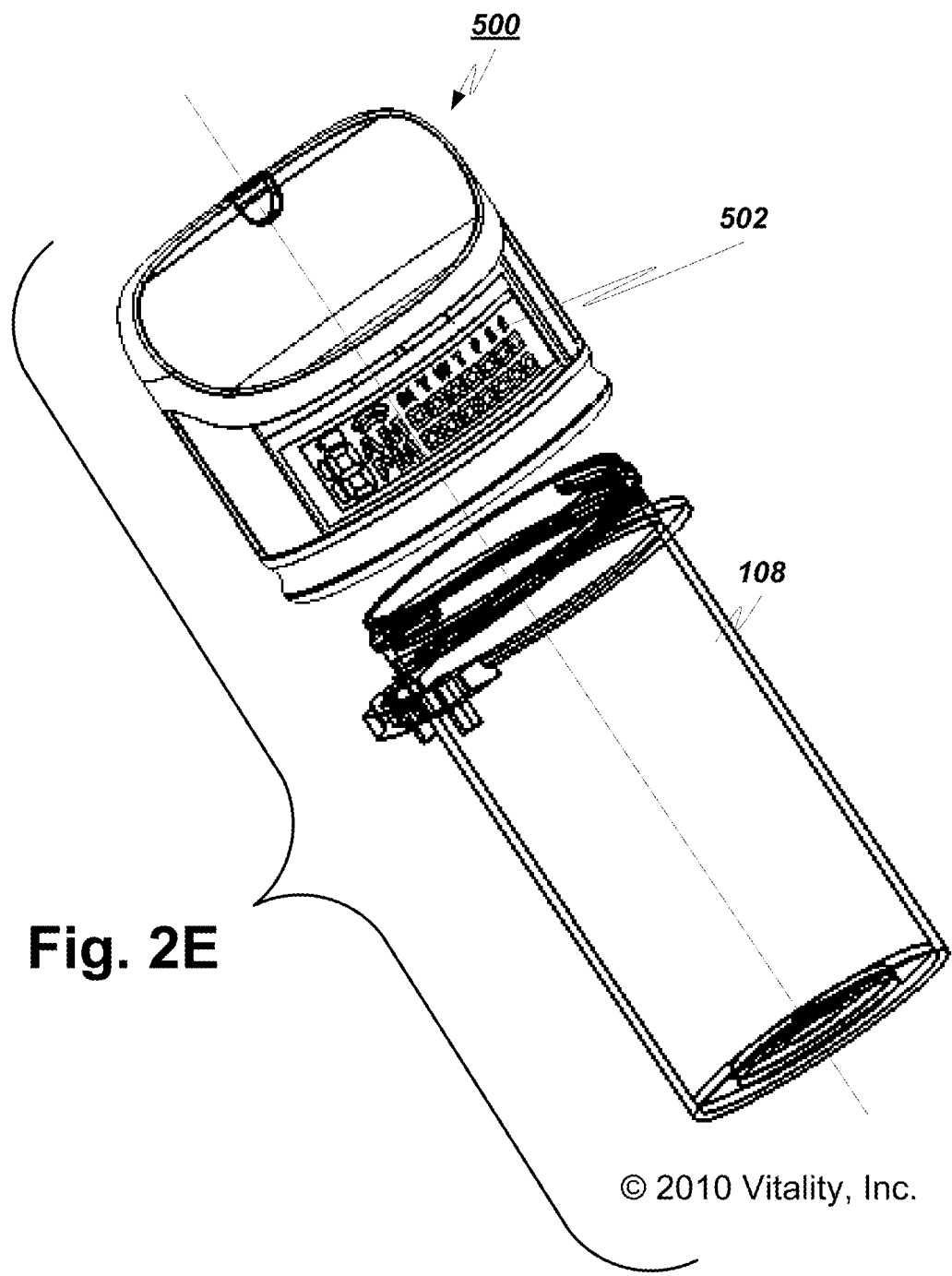
Figure 2F:
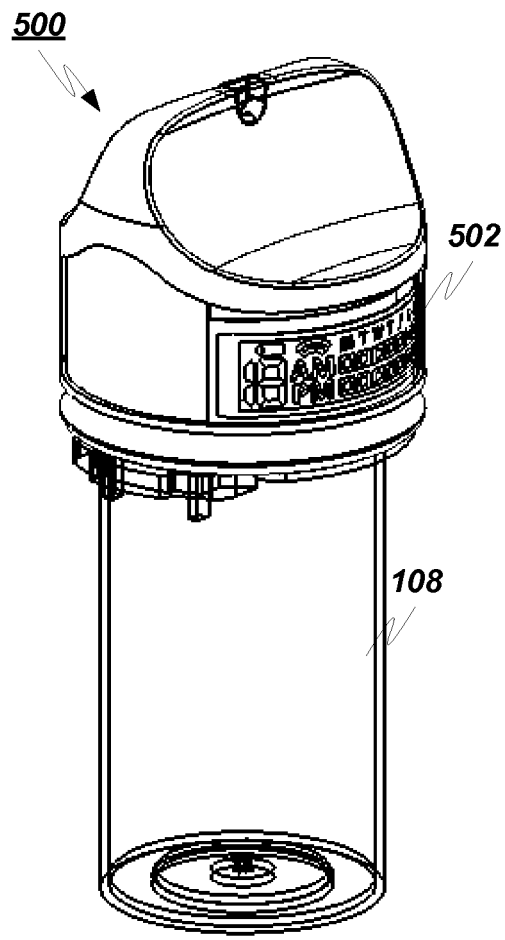
Figure 2G:
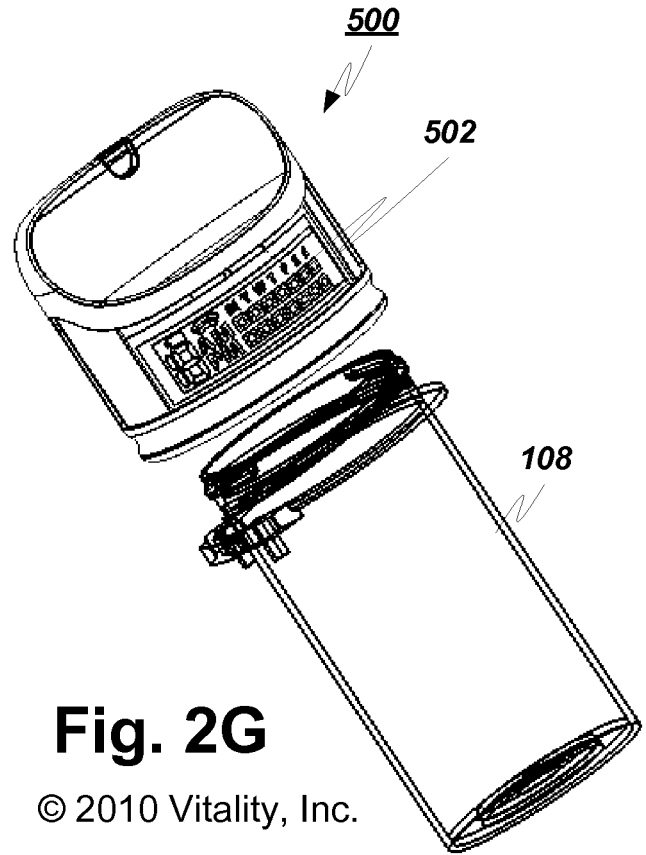
Figure 3A:
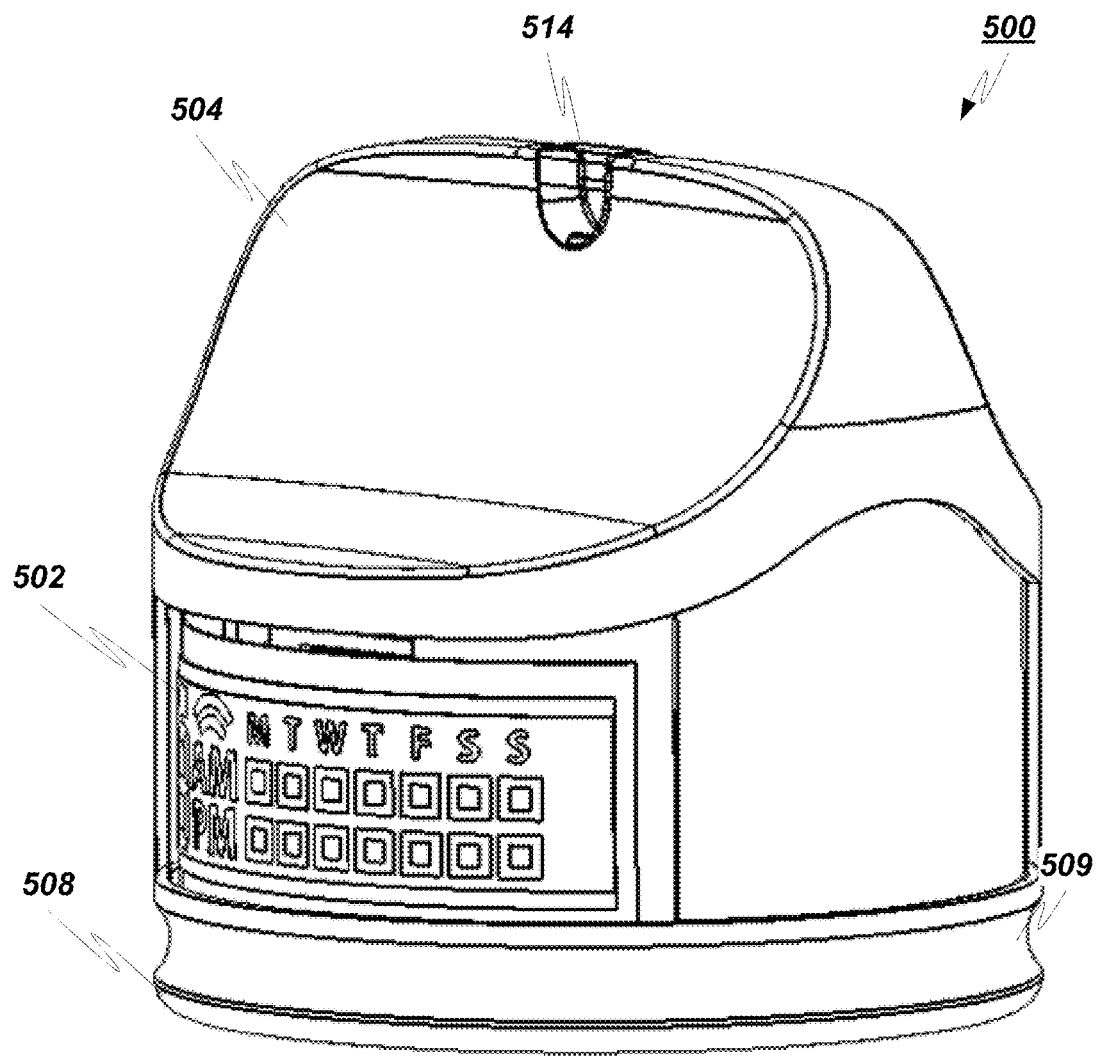
FIGS. 3A-3I are various views of an exemplary medicine bottle cap with an electronic embedded curved display.
Figure 3B:
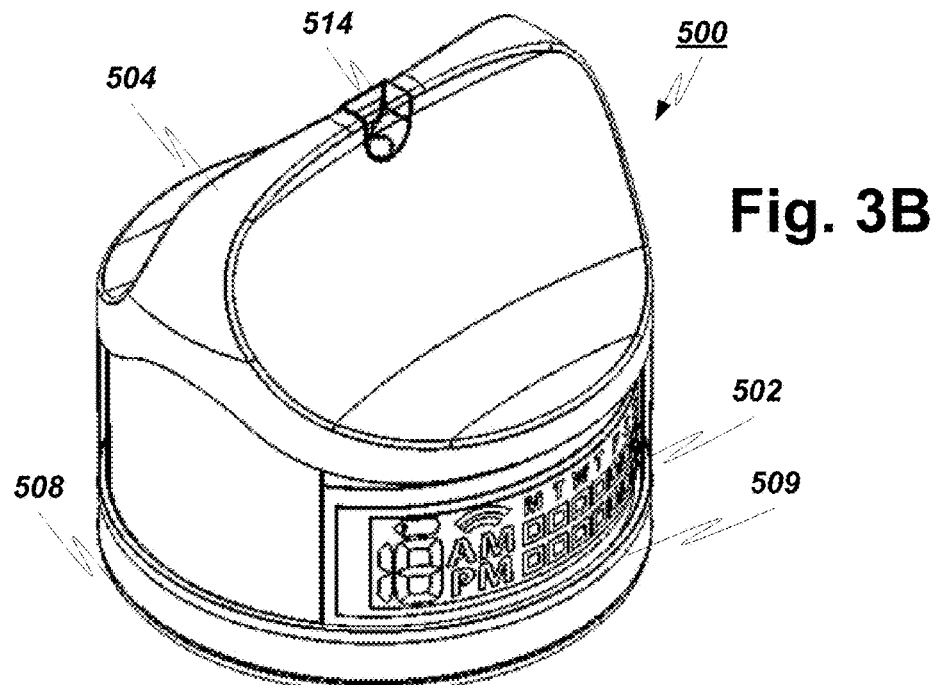
Figure 3C:
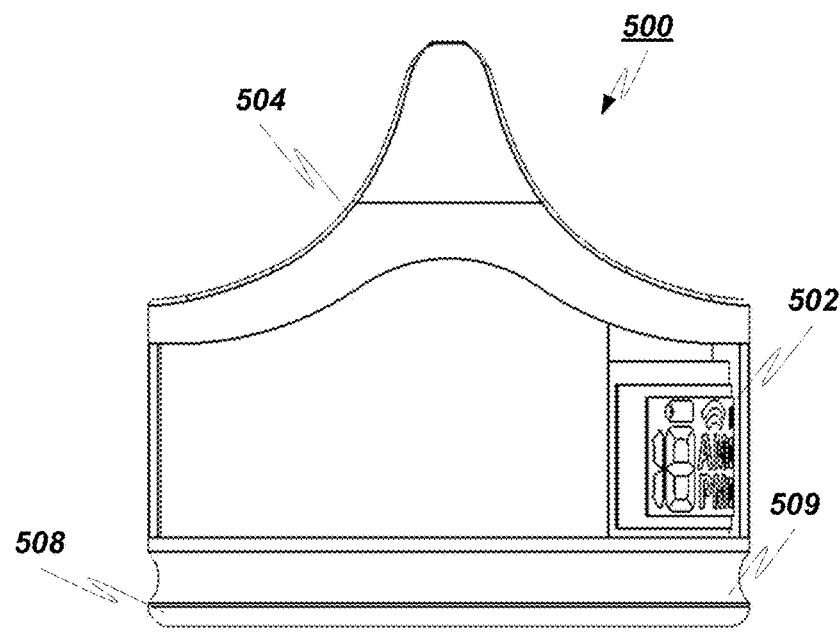
Figure 3D:
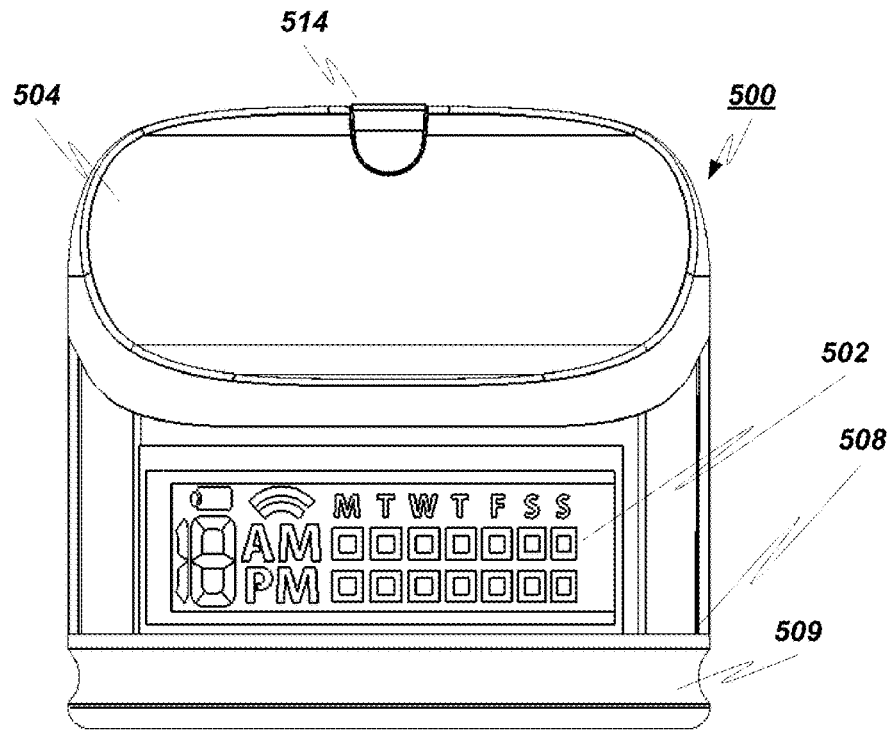
Figure 3E:
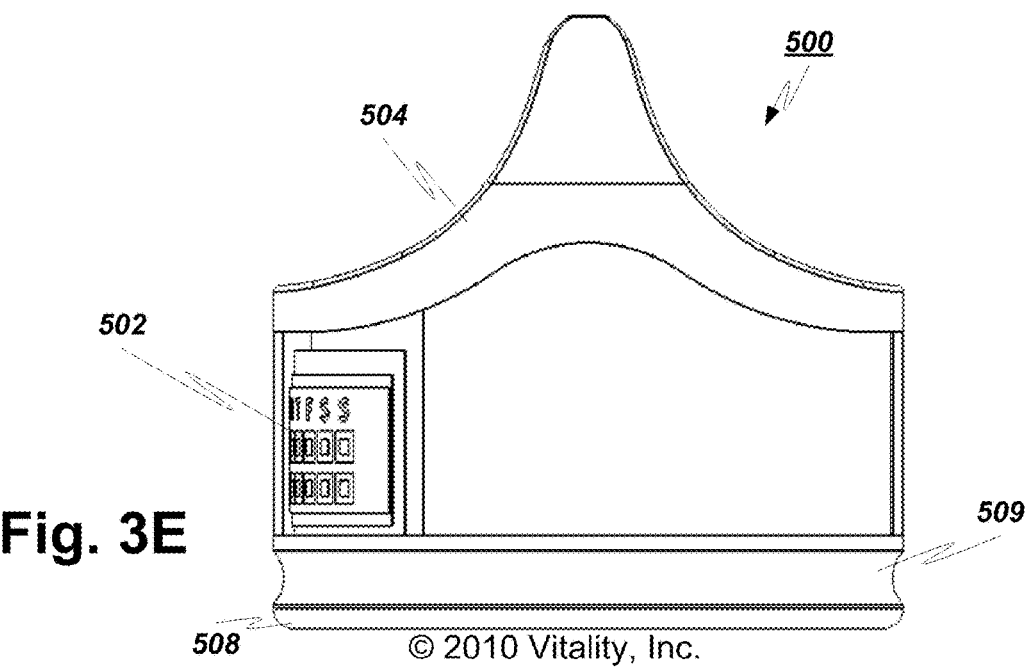
Figure 3F:
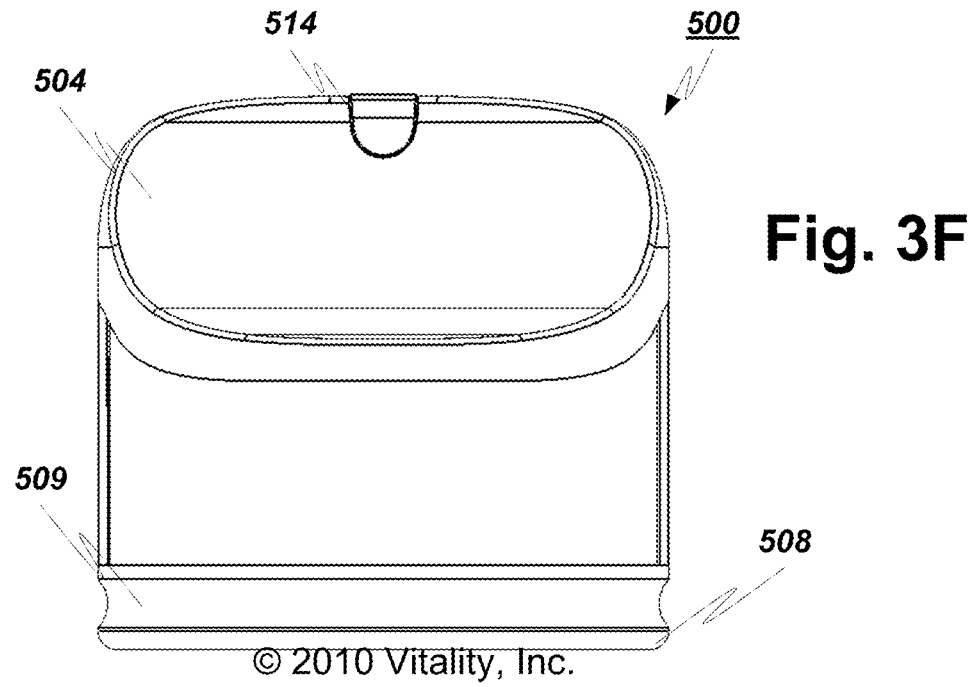
Figure 3G:
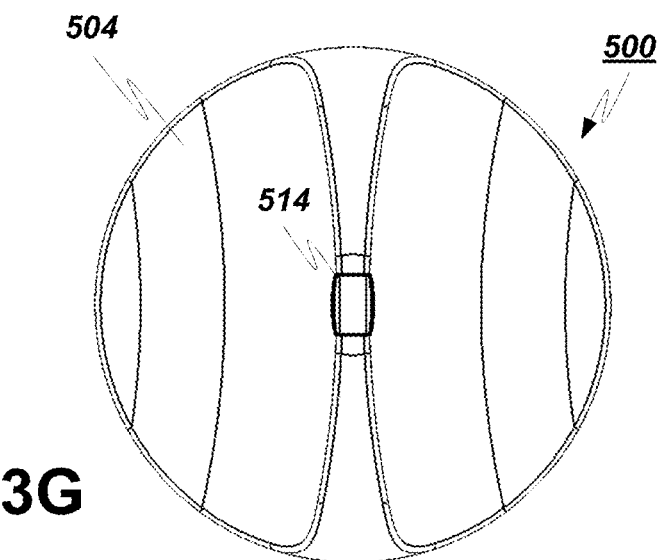
Figure 3H:
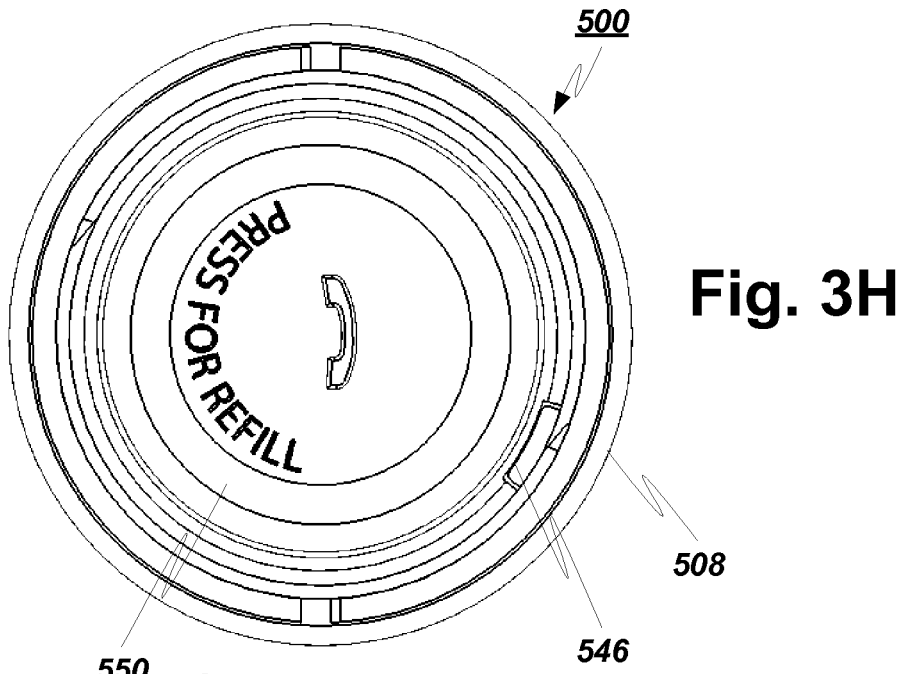
Figure 3I:
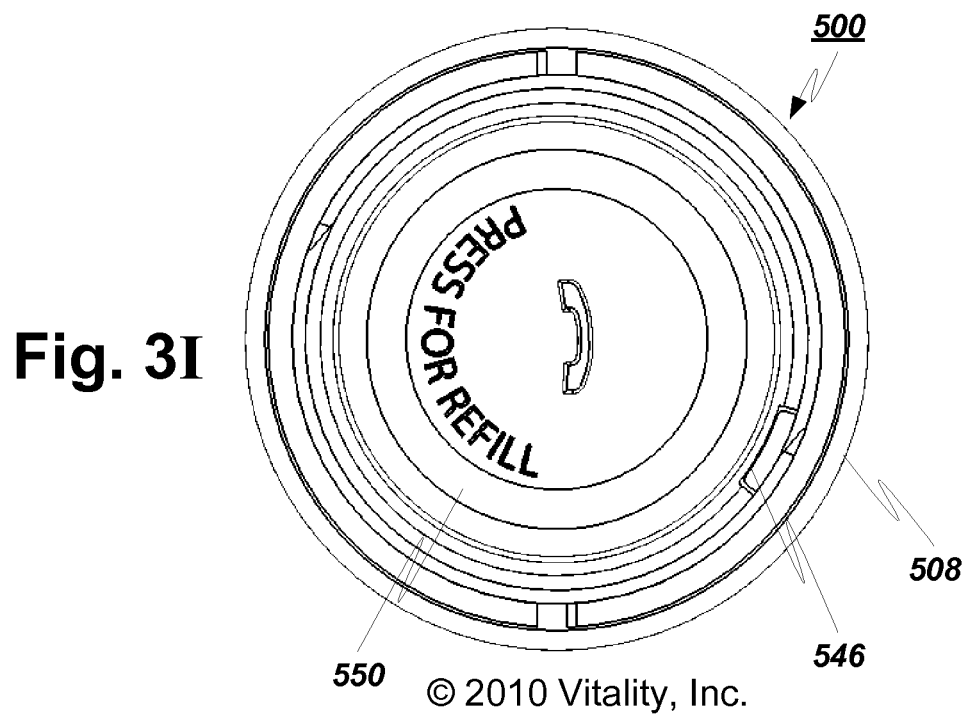
Figure 4B:
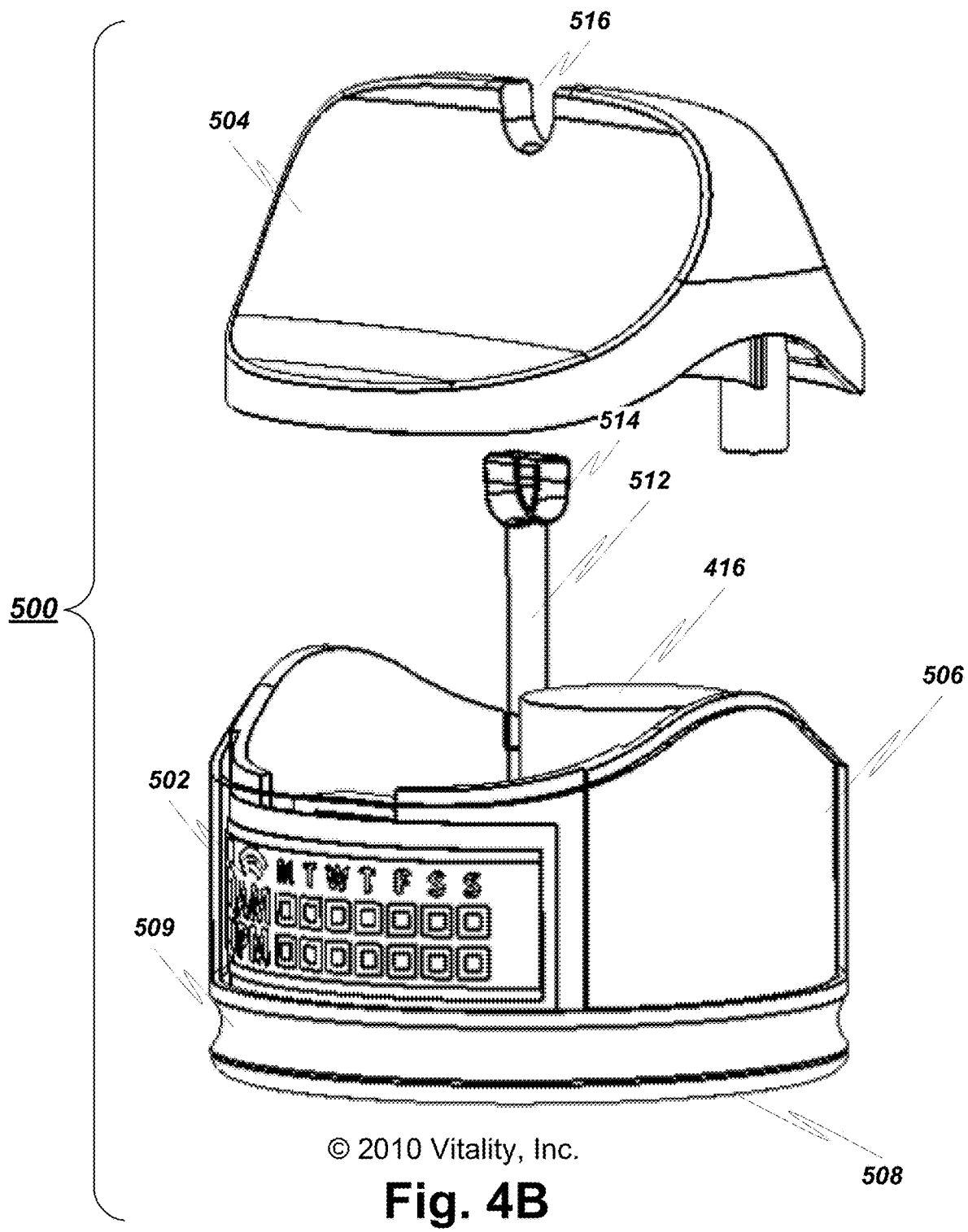
Figure 4C:
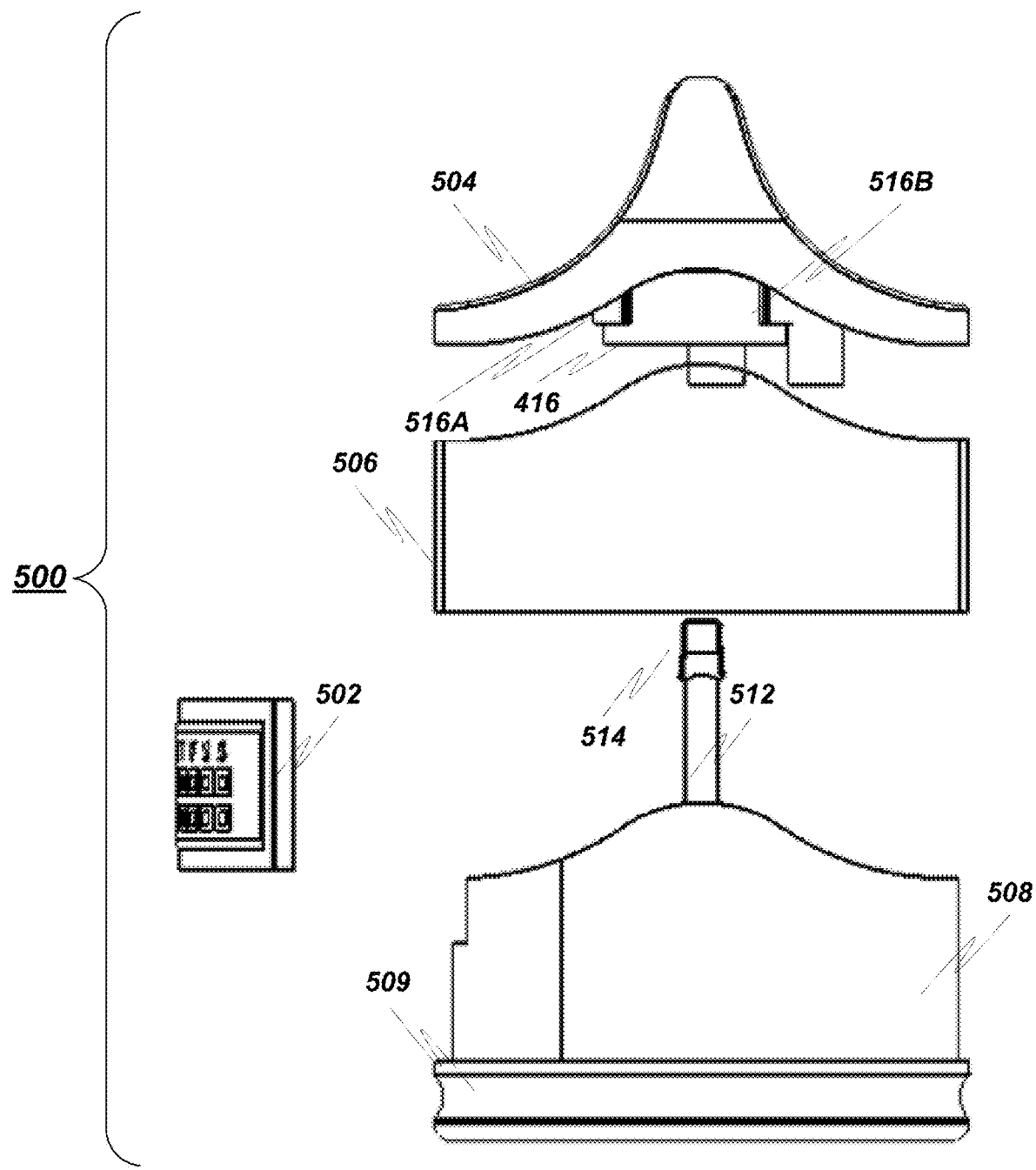
Figure 4D:
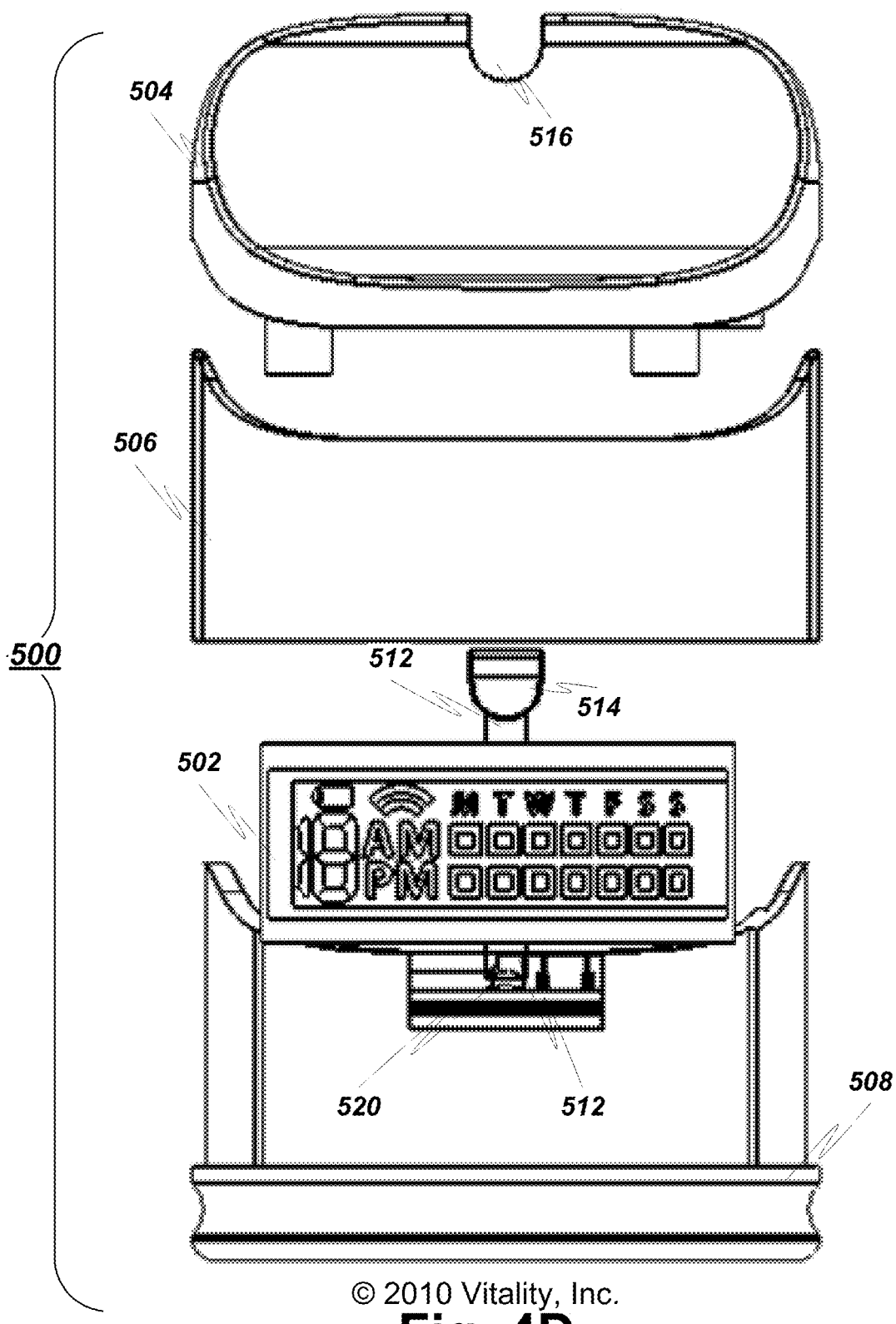
Figure 4E:
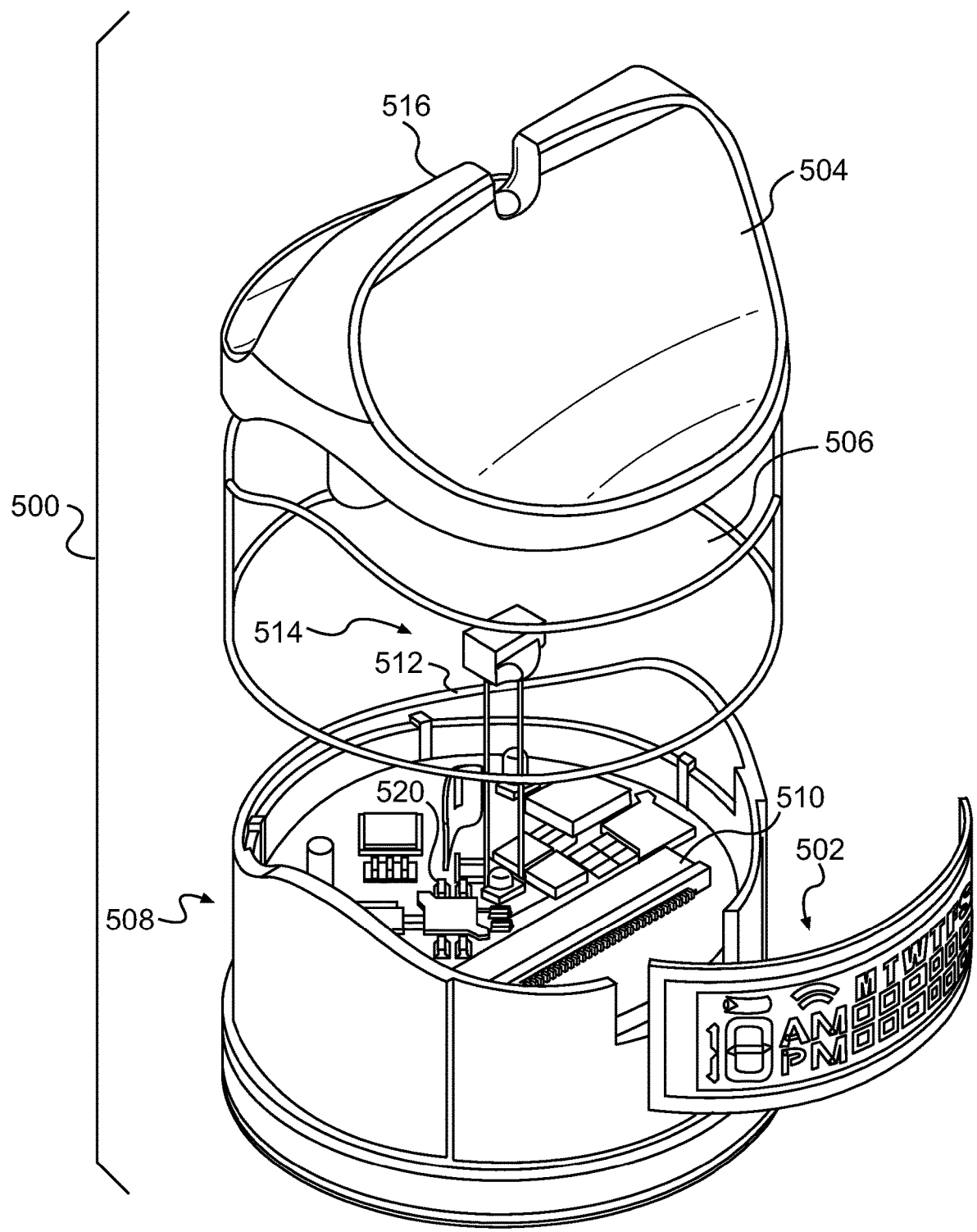

FIG. 1C is a logical diagram showing exemplary internal details of a bottle cap (corresponding to cap 110 in FIG. 1A) with an electronic embedded curved display.

With reference to the diagram in FIG. 1C, in a presently preferred implementation, the pill cap 400 includes an electronic display 402, an RF (radio frequency) transmitter/receiver 404, data store (e.g., EEPROM memory) 406, a power source such as a battery 408, a clock 413, some illumination mechanism (e.g., a tri-color LED) 410, refill button/switch 412, computational resource (computer) 414, and audio output device (e.g., a speaker) 416, a pill cap lid switch 418, a reset control 420, and appropriate circuitry which ties these components together to enable the functional behavior to take place, as described below.

A one-way pill cap only contains an RF transmitter but no receiver. It broadcasts a signal whenever it is opened and then closed within some period of time. Optionally this transmit signal may also be bundled with a payload of data which includes, battery level and a history of last dosing events (e.g., valid close times, where valid is defined to be the time between open and close is short and known) times, unique identification, etc.

A two-way pill cap 400, e.g., as depicted in FIG. 1C (includes a transmitter/receiver 404) transmits a signal whenever it is opened and closed as above. This configuration also enables the cap to receive information from another device downstream which can, e.g., (a) update the cap with new dosing regimen (revised schedule); and/or (b) check if the cap is in range; and/or (c) provided updated information for the display 402. The two-way pill cap is the preferred version, but it requires more software management (overhead) and power. The locally generated information and information received from other devices can be used to update information in the display.

Those skilled in the art will realize, upon reading this description, that different and/or other data may be provided to a one-way cap and to and from a two-way cap.

FIGS. 2A-2G show various views of medication containers 108 using a medicine bottle cap 500 (corresponding to cap 400 in FIG. 1C, cap 110 in FIG. 1A) with electronic embedded curved display 502 (corresponding to display 402 in FIGS. 1A, 1C). FIGS. 3A-3I are various views of an exemplary medicine bottle cap 500 with an electronic embedded curved display 502 (shown without the containers 108). FIGS. 4A-4E are partially exploded views of the cap 500 of FIGS. 3A-3E.

With reference to FIG. 4A, the cap 500 includes an electronic curved display 502 (corresponding to display 402 in FIG. 1C), a top cap portion 504, a clear (or optionally tinted) cover 506, and a main body 508. A board 510 and other components (such as some of those shown in FIG. 1C) are contained within the cap. A light-emitting diode (LED) 520 (corresponding to LED 410 in FIG. 1C) is positioned on the board 510, preferably in the center of the board.

Figure 5A:
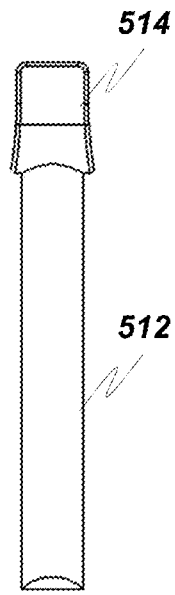
FIGS. 5A-5C are views of a light pipe used in the medicine bottle cap with an electronic embedded curved display.
Figure 5B:
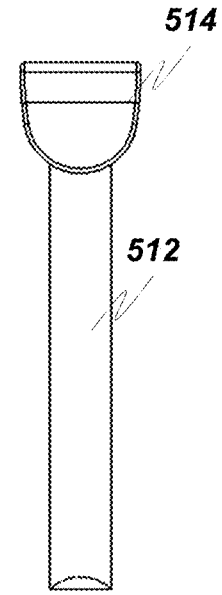
Figure 5C:
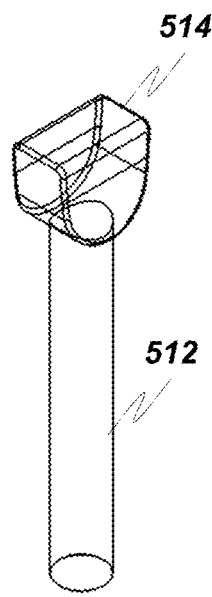

The bottle cap 500 includes a light pipe 512 (not shown in FIG. 4A) having a top portion 514. The light pipe directs light from the light-emitting diode 520 on the board 510 to the outside of the top of the cap. The top cap portion 504 includes a space 516 into which the top portion 514 of the light pipe 512 fits. An exemplary light pipe is shown in FIGS. 5A-5C. Those skilled in the art will know and understand, upon reading this description, that the shape of the light pipe depends on the position of the LED relative to the place on the outside of the cap to which the light is being directed. In the presently preferred implementation, the LED is centered on the board and the light is directed vertically, through the top center of the top portion 504.

Figure 6A:
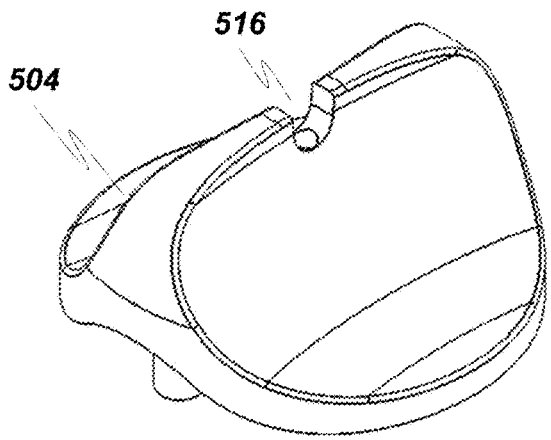
FIGS. 6A-6C are views of the top portion of the medicine bottle cap with an electronic embedded curved display.
Figure 6B:
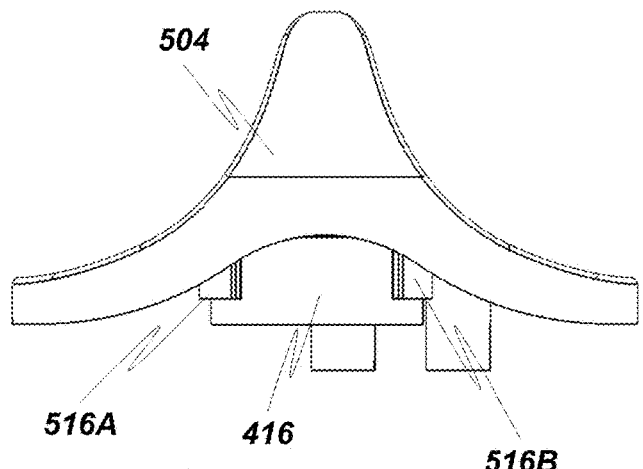
Figure 6C:
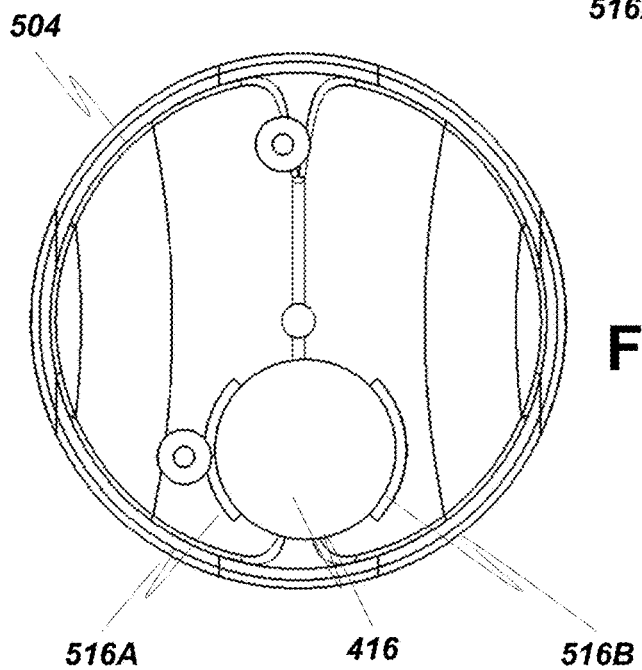

FIGS. 6A-6C are views of the top portion 504 of the cap of FIGS. 3A-3E. The top portion 504 preferably holds the speaker 416. The top portion is preferably formed of hard plastic and includes a mechanism to hold the speaker 416 in place. The speaker in these embodiments is cylindrical (as shown in the drawings), and is held in place by two side-members 516A, 516B formed in the top portion 504. In a presently preferred embodiment the speaker 416 is a cylindrical speaker made by Murata Manufacturing Co., Ltd.

FIGS. 7A-7D are views of the component board 510 of the cap 500. The component board 510 houses various components described above with reference to FIG. 1C, including the LED 520, a connector 522 for the display 502. The board 510 also includes a connecter 524 (Molex programming connector) to allow external connection to the board for programming purposes.

The board 510 also includes RF (radio frequency) transmitter/receiver 404, data store (e.g., EEPROM memory) 406, a clock 413, refill button/switch 412, computational resource (computer) 414, a reset control 420, and appropriate circuitry which ties these components together to enable the functional behavior to take place.

Figure 7A:
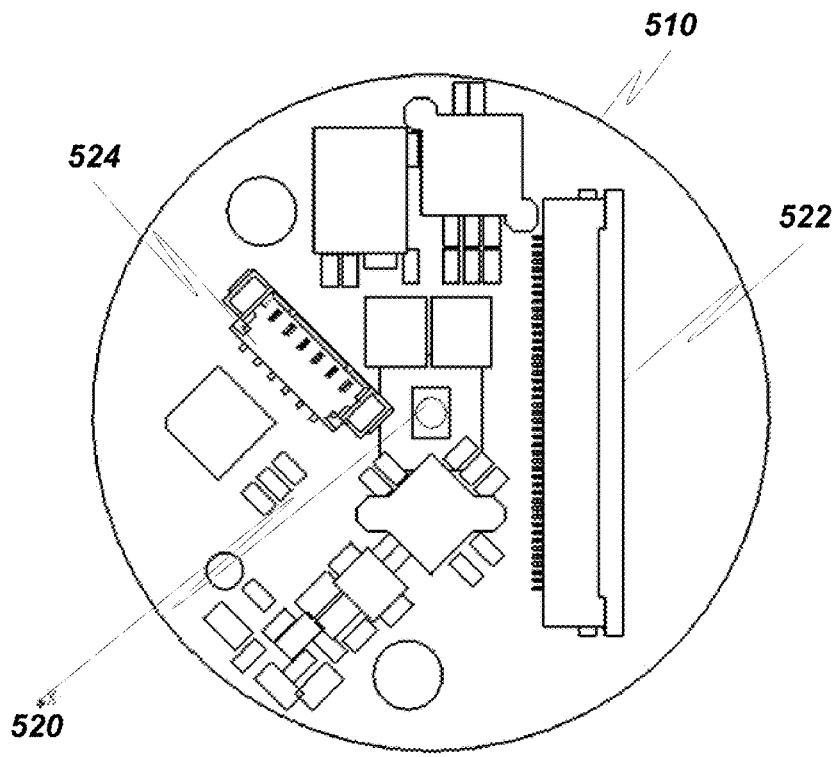
FIGS. 7A-7D are views of the component board of the medicine bottle cap with an electronic embedded curved display.
Figure 7B:
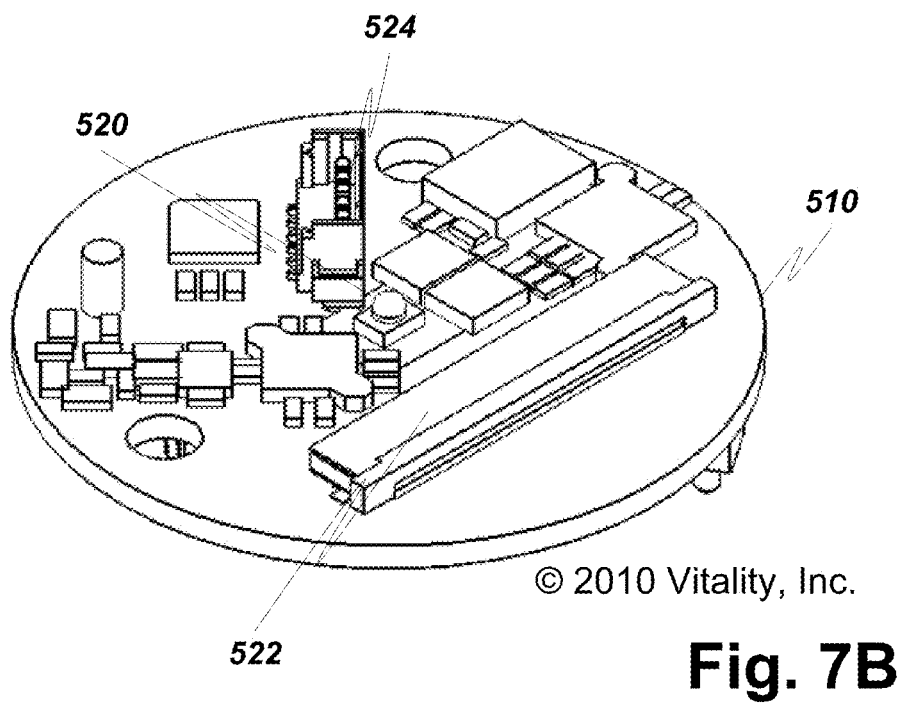
Figure 7C:
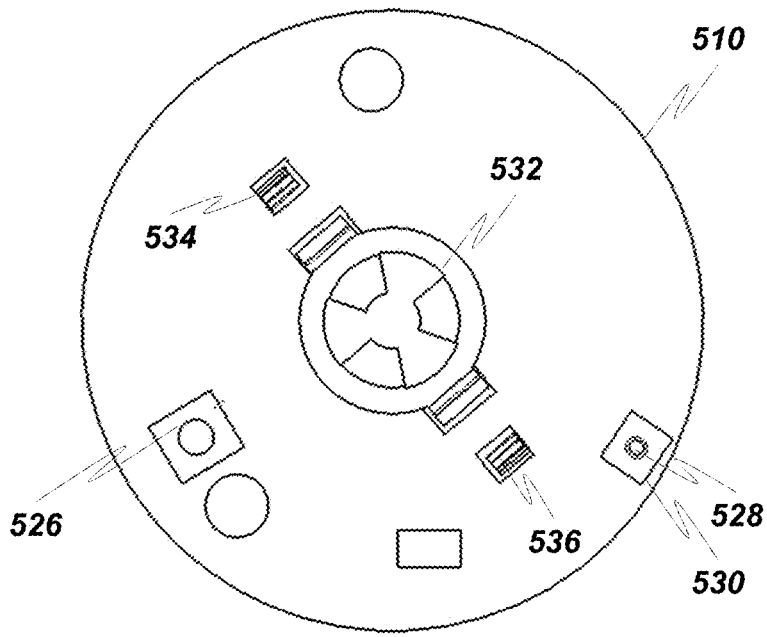
Figure 7D:
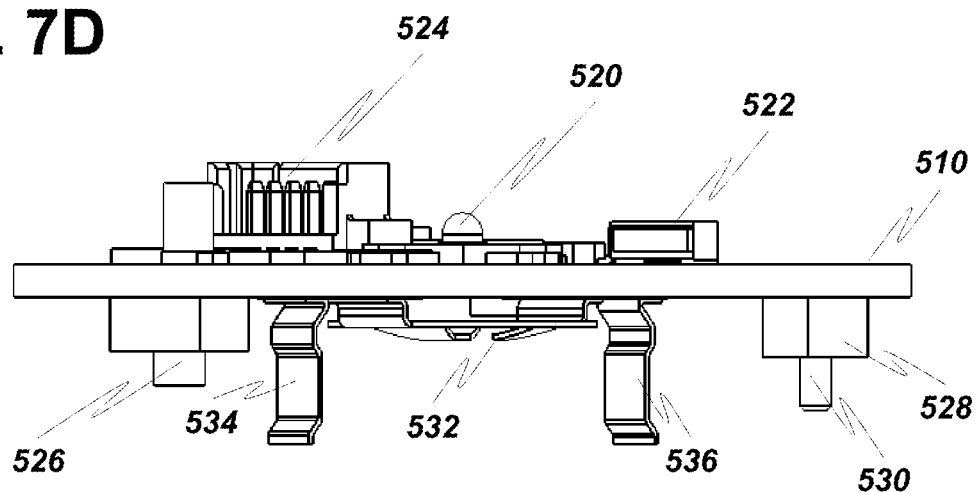

FIGS. 7C and 7D are side and bottom views of the board 510, respectively. The bottom of the board includes switch 526 (corresponding to 418 in FIG. 1C) used to detect removal of the cap from the container. Switch 528 (held inside switch body 530, and corresponding to 412 in FIG. 1C) may be used by a user to manually signal an event/request (e.g., a refill request). The underside of the board 510 also holds a center battery contact 523 and two side battery contacts 534, 536. A battery 408 is help in place against these contacts.

Figure 8A:
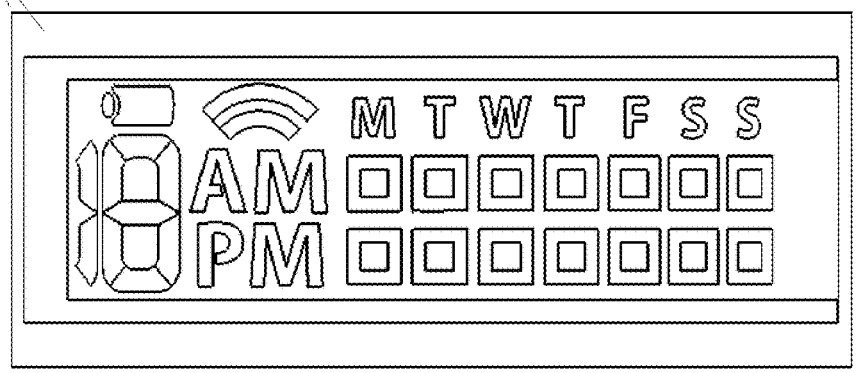
FIGS. 8A-8C shows the electronic display portion of the medicine bottle cap with an electronic embedded curved display.
Figure 8B:
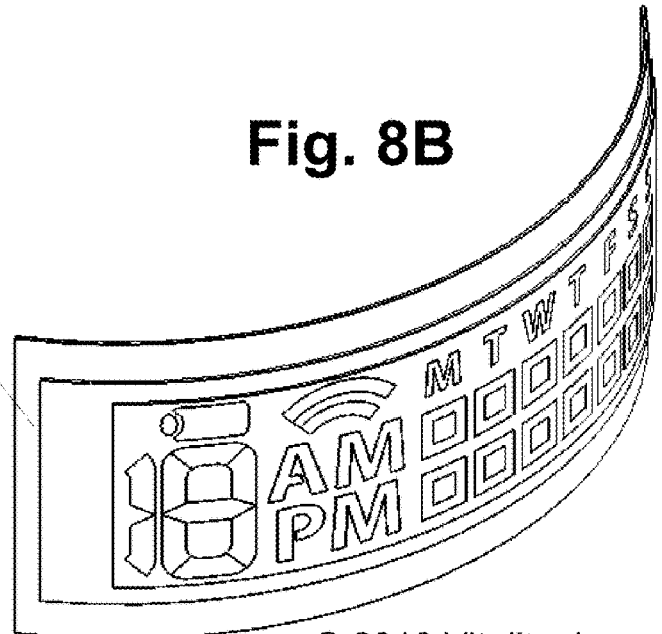
Figure 8C:
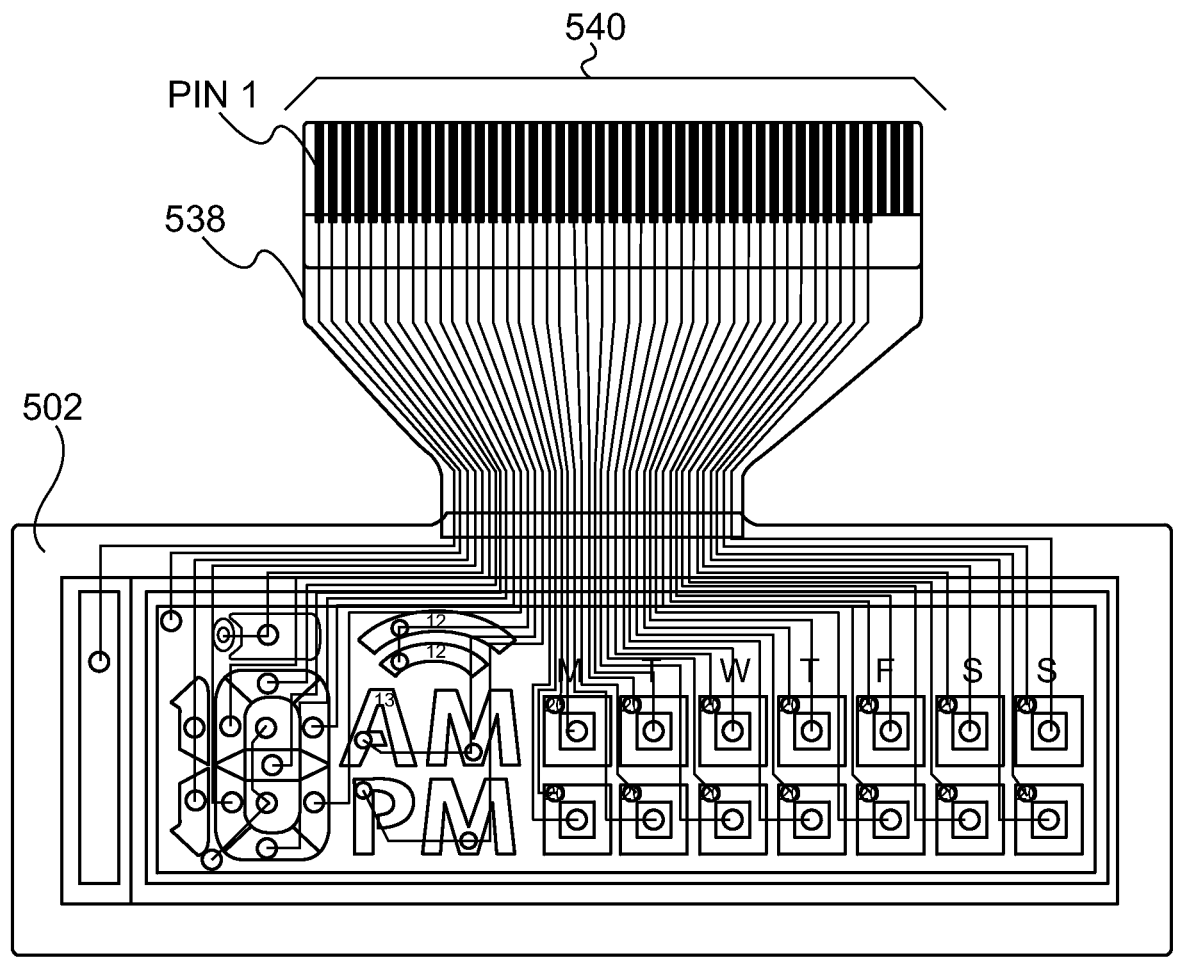

FIGS. 8A-8C show the electronic display portion of the cap of FIGS. 3A-3E. The indicia and glyphs (e.g., day, time, battery, etc.) shown in display 502 (corresponding to display 402 in FIG. 1C) in the drawings are exemplary. Those of skill in the art will know and understand, upon reading this description, that different and/or other indicia and information may be shown on the display 502.

Preferably the display 502 is a flexible display that uses ultra-low power and is easily read under any lighting condition including direct sunlight. Also, preferably the display 502 should look the same from various different viewing angles and should not distort when touched or flexed.

The display is preferably monochrome and uses a fixed set of glyphs, a so-called, segmented display, as is common in the realm of low cost liquid crystal displays. If the number of display segments is very dense, a so called dot-matrix display may be created. In this configuration, the displayed content could become a 2D bar-code readable display enabling it to also function as a machine-readable information display.

In a presently preferred implementation the display 502 is made by E Ink Corporation of Cambridge, Mass. The display 502 is flexible and so curves with the curve of the main body 508. In presently preferred embodiments, the display is about 0.375±0.020 μM thick at its thickest part.

The E Ink display features a membrane of sandwiched charged microspheres that may be rotated to indicate information by changing the charge in a fluid that surrounds the microspheres. Properties of this display that make it desirable for this invention are its extreme low power requirements, mechanical stability, wide viewing angle and sunlight readability. In addition, this invention benefits from this display technology being ultra thin, lightweight and flexible.

To control the display an array of driver wires (538 in FIG. 8C) are connected from the processor (via connector 522) to the display's backplane. In a presently preferred embodiment, this ribbon of driver wires penetrates the exterior wall of the cap to connect to the processor and related circuitry inside (via connector 522).

To maintain the curvature of the cap, the display preferably fits into a receiver channel in the base 508. To make the display appear as if it is on the exterior surface of the cap and not protruding from that surface, a shallow bezel may receive the display so that its top surface shares a common radius with the cylindrical caps exterior. Accordingly, an appropriate indent is preferably formed in the main body 508 to hold the display in place against the body.

To protect the display from damage due to handling, etc., a optionally transparent, wrapper (clear portion 506) covers the display. This wrapper may be selectively tinted as a pneumonic device for the cap owner to recognize which medicine is in the container using the cap. E.g., the transparent wrapper may be tinted a color (e.g., such as red) to help the user identify the medication. Accordingly, the clear portion 506 fits over the display and main body and keeps the display in place and protects it.

The presently preferred connector 522 is a 45-contact connector made by FCI (part number 62684-451100ALF).

While the display is shown in the drawings as going around only a part of the main body (and thus the cap), those of skill in the art will appreciate and understand, upon reading this description, that the display can have different dimensions in length and height, and that the display can cover a greater or smaller portion of the cap. In addition, while the cap is shown with only one display, those of skill in the art will appreciate and understand, upon reading this description, that more than one display can be used, though each display could require its own connector on the board 510.

FIG. 8C shows the connector wiring 538 used to connect the display 502 to the connector 522 on the board 510, and the following table (Table 1) summarizes the wiring of the pins 540 with respect to the connector 522 in a current implementation. (The pins 540 in FIG. 8B are numbered 1-45, from left to right.)

TABLE 1

| Pin | Segment description |
|---|---|
| 1 | top plane |
| 2 | Field |
| 3 | One |
| 4 | Bottom left |
| 5 | Battery |
| 6 | Top left |
| 7 | Top |
| 8 | Middle |
| 9 | Bottom |
| 10 | Top right |
| 11 | Bottom right |
| 12 | Antenna signal |

TABLE 1-continued

| Pin | Segment description |
|---|---|
| 13 | AM |
| 14 | PM |
| 15 | "M" bottom middle |
| 16 | "M" bottom outside |
| 17 | "M" top outside |
| 18 | "M" top middle |
| 19 | "T" bottom middle |
| 20 | "T" bottom outside |
| 21 | "T" top outside |
| 22 | "T" top middle |
| 23 | "W" bottom middle |
| 24 | "W" bottom outside |
| 25 | "W" top outside |
| 26 | "W" top middle |
| 27 | "T" Bottom middle |
| 28 | "T" Bottom outside |
| 29 | "T" top outside |
| 30 | "T" top middle |
| 31 | "F" bottom middle |
| 32 | "F" bottom outside |
| 33 | "F" top outside |
| 34 | "F" top middle |
| 35 | "S" bottom middle |
| 36 | "S" bottom outside |
| 37 | "S" top outside |
| 38 | "S" top middle |
| 39 | "S" Bottom middle |
| 40 | "S" bottom outside |
| 41 | "S" top outside |
| 42 | "S" top middle |

Pins 43, 44, 45 have no connection

The mapping of the pins shown in Table 1 above is implementation dependent. Thus, while a specific wiring to the indicia/components in the display is shown in the drawing, those of skill in the art will know and understand, upon reading this description, that different and/or other wiring may be used, depending on the display.

Figure 9A:
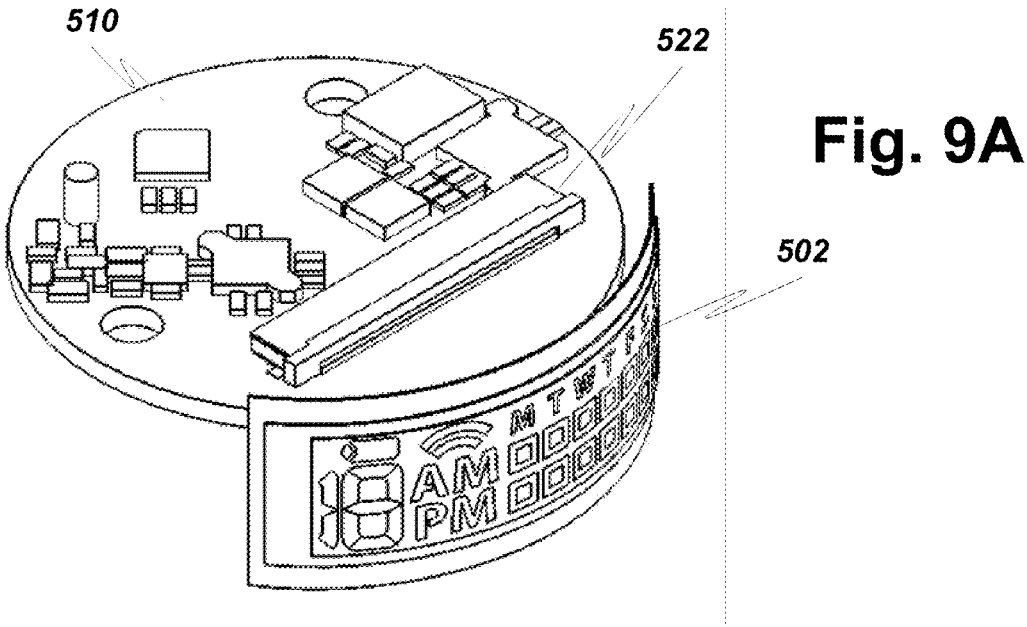
FIGS. 9A-9B show the display positioned relative to the board and connector.
Figure 9B:
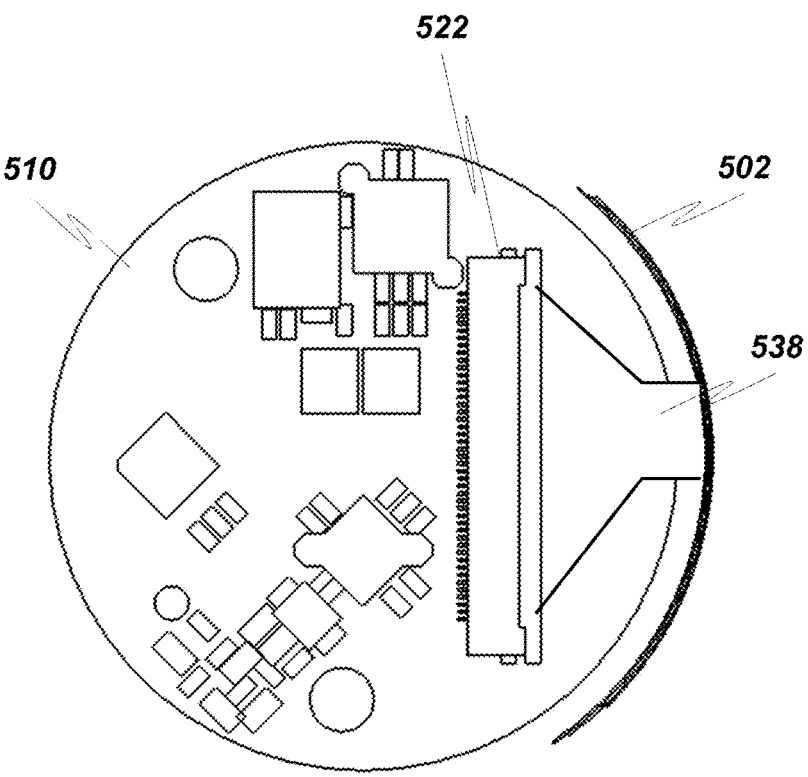

FIGS. 9A-9B show the display 502 positioned relative to the board 510 and connector 522 with wires 538 electronically connecting the display to the connector.

Figure 10A:
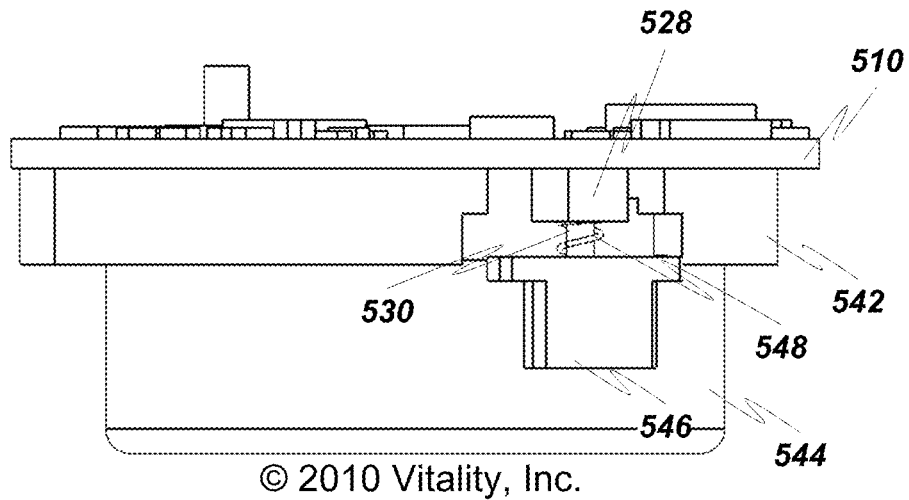
FIGS. 10A-10B are views of an interface component of the medicine bottle cap with an electronic embedded curved display.
Figure 10B:
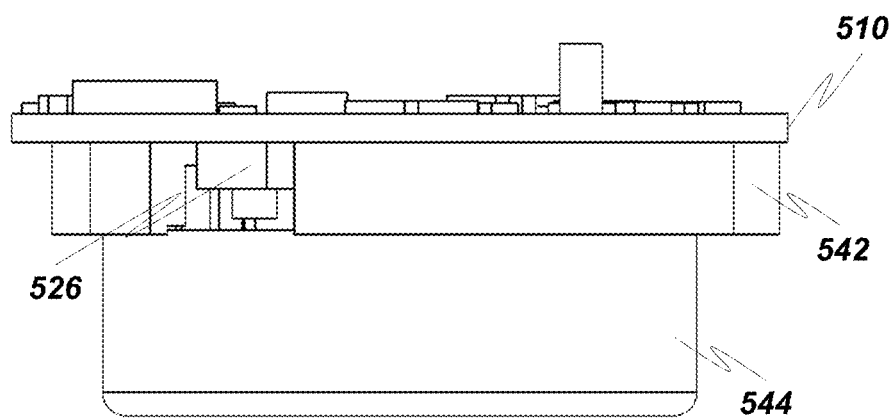

FIGS. 10A-10B are views of an interface component 542 of the cap 500 of FIGS. 3A-3E. The interface component 542 is positioned under the board 510 to position the battery (not show) against the underside of the board and to hold various components. A battery cover 544 holds the battery in place.

Figure 11A:
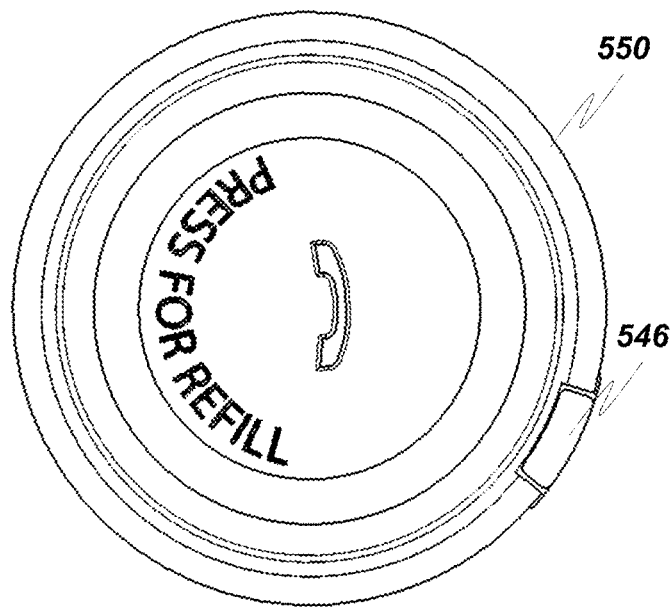
FIGS. 11A-11B are bottom and side views, respectively, of a gasket used in the medicine bottle cap with an electronic embedded curved display.
Figure 11B:
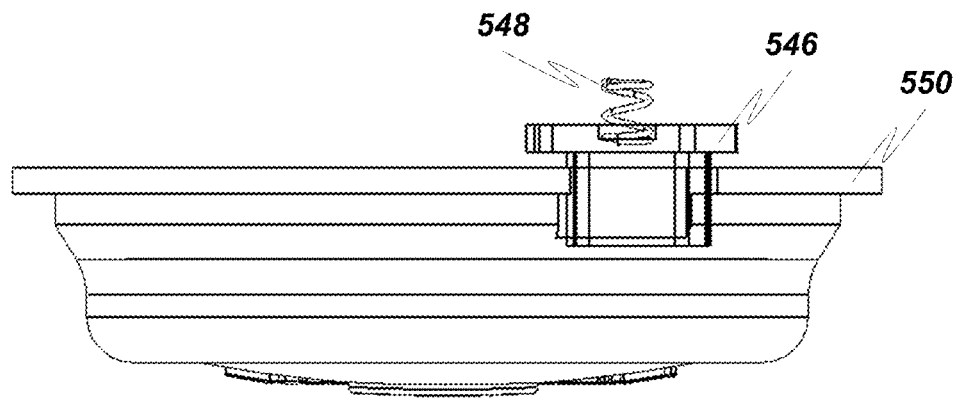
Figure 12:
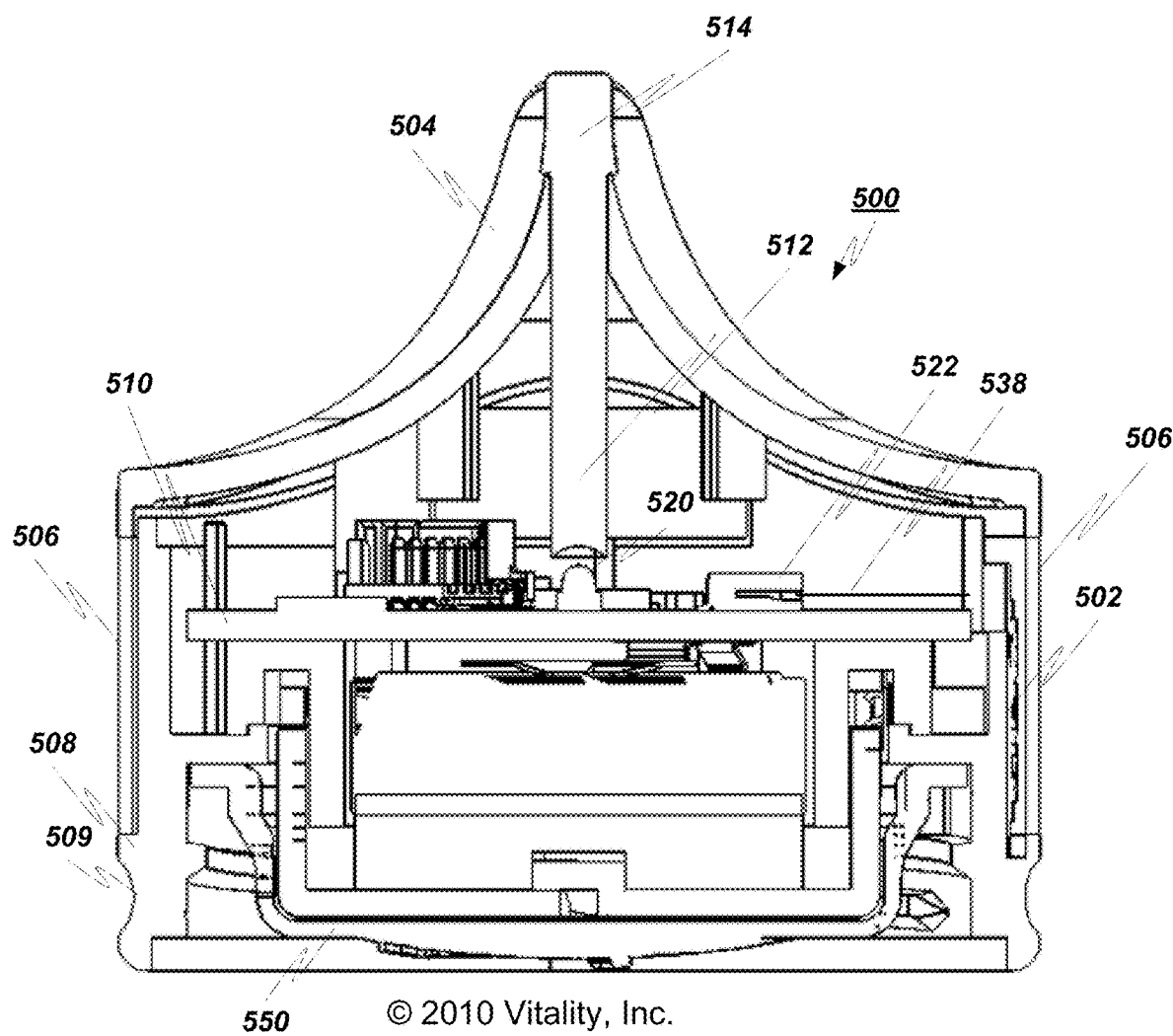
FIG. 12 is a cross-sectional view of the medicine bottle cap with an electronic embedded curved display.

Switch 528 (corresponding to 412 in FIG. 1C) held inside switch body 530) may be used by a user to manually signal an event/request (e.g., a refill request). A spring 548 keeps button 546 from depressing the switch 528 without appropriate pressure. A gasket 550 covers the batter (not shown in FIG. 10A, shown in FIGS. 11A-11B), engages the button 546 so that when the gasket is depressed by a user, the button 546 depresses the switch 528.

FIGS. 2A-2G show various views of medication containers using a medicine bottle cap with electronic embedded curved display. While a particular connector system (for connecting the caps to bottles) is shown. Those skilled in the art will realize and understand, upon reading this description, that the actual mechanical interlock mechanism (e.g., screw, bayonet mount, snap-on, etc.) used with each cap will depend on the size and kind of medicine bottle as well as the bottle's interlock system. In some embodiments, an adaptor may be provided to allow caps for one kind of bottle to fit on another kind of bottle.

The main body main include an indented circular portion 509. This portion may be color coded to provide additional information to the patient.

The patient's medication is provided in a container with a cap. The container may be a regular container or may be specifically adapted to operate with the cap. Those of skill in the art will understand, upon reading this description, that the container/cap combination can be used with any medication delivery system and with any type of medication, regardless of its form or dosage. The cap may be fully or partially removable or fully or partially openable, or it may be an integral part of the container through which medication is dispensed.

Those of skill in the art will realize, upon reading this description, that the container/cap combination may take any form, as long as the system can detect when medication was likely or possibly dispensed.

In a preferred embodiment the pill cap includes a light sensor that can detect changes in ambient illumination. This is part of a further battery saving scheme that enables the illuminator to turn off if the container is stored in a dark place. Patients often store their medication in a closed cabinet or drawer (much medication should be stored in a dark place) and there is no reason to deplete battery illuminating the feedback signal if no one can see it. In this scenario the pill cap immediately gives visual indication that it is dose time ("its me" (as opposed to the other caps for which it is not time to dose now)) if dose time has occurred and the ambient light sensor has indicated a change (suggesting it is in view of patient). The ambient light sensor could be replaced with or supplemented with a motion sensor.

In some embodiments, the sensor also detects that the correct medication dose was actually removed from the container.

The display 502 embedded in the cap can provide textual and other visual feedback to the patient. Data on display 502 may instruct the patient which dose (afternoon/morning, etc.), which pill (shape, color, size) needs to be taken.

The cap includes local data memory and permanent memory. The device preferably includes a "store and forward" architecture to ensure data collected on it has a physical location in which to reside if an upload network connection is not possible for some period of time.

A smart cap version provides interoperable mounting rings or bases to the cap. If needed, coupling rings are provided to enable one type of smart cap to mount to any of a variety of commercially available bottles of near similar opening diameter. This avoids having to develop custom caps for each bottle and enables patients to take this platform and use it for medications provided in vials sold by disparate retail pharmacies.

Thus is described a bottle cap having an embedded electronic display that curves around the cap's exterior. The cap is operable in service of promoting medication adherence with a novel feedback loop, e.g., as described in the related patent applications which have been incorporated herein by reference. A cap preferably includes at least the following functional components:

battery,
processor,
open/close switch,
some mechanism for keeping time; and
the curved electronic display.

The display may provide useful information, e.g., an indication of whether the cap has been opened and may optionally indicate a schedule of past open events or indicate future events. The display may also display other information such as, e.g., instructions, medicine name, battery level, time, network connectivity strength (if RF connectivity is also embedded in the cap), patient name, availability of rewards, financial incentives, social network status, who the data is shared with or other such medically relevant information.

In a preferred embodiment, the cap also has network connectivity via standard means (local RF or intermittently via physical connector). In this configuration, among other messages, e.g., the display may indicate environmental conditions such as pollen forecast for allergy related medication, biometrics such as blood pressure for hypertension patients or whether a refill is pending pickup or has been ordered.

As used herein, the term "medication" refers to any kind of medicine, prescription or otherwise. Further, the term "medication" includes medicine in any form, including, without limitation pills, salves, creams, powders, ointments, capsules, injectable medications, drops, vitamins and suppositories. The scope of this invention is not limited by the type, form or dosage of the medication.

Although aspects of this invention have been described with reference to a particular system, the present invention operates on any computer system and can be implemented in software, hardware or any combination thereof. When implemented fully or partially in software, the invention can reside, permanently or temporarily, on any memory or storage medium, including but not limited to a RAM, a ROM, a disk, an ASIC, a PROM and the like.

While certain configurations of structures have been illustrated for the purposes of presenting the basic structures of the present invention, one of ordinary skill in the art will appreciate that other variations are possible which would still fall within the scope of the appended claims. While the invention has been described in connection with what is presently considered to be the most practical and preferred embodiment, it is to be understood that the invention is not to be limited to the disclosed embodiment, but on the contrary, is intended to cover various modifications and equivalent arrangements included within the spirit and scope of the appended claims.

We claim:

1. A cap for a medicine container, the cap comprising:
   a base portion having a curved outer surface and being connectable to a medicine container;
   a top portion coupled to the base portion and having a pair of opposed surfaces extending toward each other from opposed regions of the base portion;
   a light emitting diode (LED) disposed within the base portion and electrically coupled with circuitry within the base portion; and
   a light pipe in optical communication with the LED, the light pipe forming a portion of each of the pair of opposed surfaces of the top portion and being capable of directing light from the LED and through the portion of each of the pair of opposed surfaces defined by the light pipe.

2. The cap of claim 1 being connectable to a medicine container selected from the group consisting of the following: a bottle, a pill box, a salve tube, a syringe, and an inhaler.

3. The cap of claim 1 further comprising:
   an RF transmitter/receiver disposed within the base portion and electronically coupled with the circuitry.

4. The cap of claim 1 further comprising:
   a speaker disposed within the base portion and electronically coupled with said circuitry.

5. The cap of claim 1, wherein the LED is a multi-color LED.

6. The cap of claim 1, further comprising at least one switch disposed within the cap and electronically coupled with the circuitry.

7. The cap of claim 6, further comprising a button disposed on a bottom portion of the cap and mechanically coupled with at least one switch.

8. The cap of claim 6, wherein the at least one switch detects removal of the cap from the medicine container.

9. The cap of claim 6, wherein the at least one switch allows manual signaling of an event via the circuitry.

10. The cap of claim 9, wherein the event comprises a refill request sent via the circuitry.

11. The cap of claim 1, wherein the display comprises flexible driver wires configured to couple with a connector of the circuitry.

12. The cap of claim 1, wherein the circuitry is operative to provide visual feedback via the display according to a medication regime.

13. The cap of claim 1, wherein each of the opposed surfaces of the top portion defines an externally concave configuration.

14. The cap of claim 1, wherein the top portion further includes a top surface positioned between the pair of opposed surfaces.

15. The cap of claim 1, further comprising:
a flexible electronic e-ink display fitting in the display receiving channel of the base portion forming a curved display surface that follows the curvature of the base portion, and electronically coupled with circuitry within the cap, wherein the e-ink display comprises a membrane of sandwiched charged rotatable microspheres; and
a clear cover covering the electronic display.

16. The cap of claim 15 wherein the electronic display is about 0.375 μm thick at its thickest part.

17. The cap of claim 15 wherein the clear cover is tinted with a color.

18. The cap of claim 15, wherein the curved display surface goes around at least part of a perimeter of the base portion.

19. The cap of claim 18, wherein the curved display surface goes around a perimeter of the base portion.

20. The cap of claim 15, further comprising a second electronic display distinct from the flexible electronic display, the second electronic display coupled with the circuitry.

* * * * *